United States Patent
Winfree et al.

(10) Patent No.: US 10,670,394 B2
(45) Date of Patent: Jun. 2, 2020

(54) SYSTEM AND METHOD FOR DETERMINING THE DIRECTION AND SPACING OF FIBER PATHS FOR A COMPOSITE PLY

(71) Applicant: The Boeing Company, Chicago, IL (US)

(72) Inventors: Troy Winfree, Tukwila, WA (US); Adriana Willempje Blom-Schieber, Seattle, WA (US)

(73) Assignee: The Boeing Company, Chicago, IL (US)

( * ) Notice: Subject to any disclaimer, the term of this patent is extended or adjusted under 35 U.S.C. 154(b) by 456 days.

(21) Appl. No.: 15/634,837

(22) Filed: Jun. 27, 2017

(65) Prior Publication Data

US 2018/0372488 A1 Dec. 27, 2018

(51) Int. Cl.
*G01B 21/16* (2006.01)
*G06F 30/20* (2020.01)
(Continued)

(52) U.S. Cl.
CPC ............ *G01B 21/16* (2013.01); *B29C 70/382* (2013.01); *B29C 70/386* (2013.01); *B29C 70/54* (2013.01);
(Continued)

(58) Field of Classification Search
CPC ..... B29C 70/382; B29C 70/386; G01B 21/16; G06F 17/5095; G06F 2217/42; G06F 2217/44
See application file for complete search history.

(56) References Cited

U.S. PATENT DOCUMENTS 8,557,074 B2   10/2013   McCowin
8,756,037 B2    6/2014   Rassaian
(Continued)

OTHER PUBLICATIONS

European Patent Office, Examination Report for Appl. No. 18171129.2-1224, dated Jan. 29, 2019.
(Continued)

*Primary Examiner* — Catherine T. Rastovski

(57) ABSTRACT

A method of determining fibers paths for a composite ply includes generating a triangulated surface of the composite ply, and defining a first unit vector field establishing a 0-degree direction for the triangulated surface. A second unit vector field is defined by rotating, through specified fiber angles measured relative to the 0-degree direction, the first unit vector field about surface normals of the triangulated surface. A third unit vector field representing a gradient direction of a potential function is defined by rotating the second unit vector field over 90° about the respective surface normals. The third unit vector field is scaled to create a non-unit vector field, and a first potential function is determined by performing a least-squares fit such that the direction and magnitude of the gradient best approximate the direction and the magnitude of the non-unit vector field. A normalization of the potential function uniformly distributes contour lines of the potential function across the triangulated surface. The contour lines are used as fiber paths for laying up courses of composite material to fabricate the composite ply.

20 Claims, 22 Drawing Sheets

(51) Int. Cl.
| | |
|---|---|
| B29C 70/38 | (2006.01) |
| B29C 70/54 | (2006.01) |
| G01N 33/36 | (2006.01) |
| G06F 30/15 | (2020.01) |
| G06F 111/10 | (2020.01) |
| G06F 113/24 | (2020.01) |
| G06F 113/26 | (2020.01) |
| G06F 119/18 | (2020.01) |
| B29K 105/08 | (2006.01) |

(52) U.S. Cl.
CPC ........... *G01N 33/367* (2013.01); *G06F 30/20* (2020.01); *B29K 2105/0881* (2013.01); *G06F 30/15* (2020.01); *G06F 2111/10* (2020.01); *G06F 2113/24* (2020.01); *G06F 2113/26* (2020.01); *G06F 2119/18* (2020.01)

(56) References Cited

U.S. PATENT DOCUMENTS

| | | | | |
|---|---|---|---|---|
| 2012/0323538 A1* | 12/2012 | Rassaian | ............ | G06F 17/5018 703/2 |
| 2014/0288893 A1* | 9/2014 | Blom | ................. | G06F 17/5018 703/1 |
| 2016/0121558 A1* | 5/2016 | Munaux | ............ | G05B 19/4097 700/97 |

OTHER PUBLICATIONS

Guanxin Huang et al: "An efficient reanalysis assisted optimization for variable-stiffness composite design by using path functions", Composite Structures, Elsevier Science Ltd, GB, vol. 153, Jun. 21, 2016, pp. 409-420.

S. Honda et al: "Vibration design of laminated fibrous composite plates with local anisotropy induced by short fibers and curvilinear fibers", Composite Structures, Elsevier Science Ltd, GB, vol. 93, No. 2, Jan. 1, 2011, pp. 902-910.

Christopher J. Brampton et al: "New optimization method for steered fiber composites using the level set method", Structural and Multidisciplinary Optimization, Springer Berlin Heidelberg, Berlin/Heidelberg, vol. 52, No. 3, May 14, 2015, pp. 493-505.

EPO, EP Search Report, Appl. No. EP 18171129, dated Dec. 5, 2018.

Setoodeh, Generating Curvilinear Fiber Paths from Lamination Parameters Distribution, 47th AIAA/ASME/ASCE/AHS/ASC Structures, Structural Dynamics, and Materials Conference, Newport, Rhode Island, May 2006.

Setoodeh, "Design of variable-stiffness laminates using lamination parameters," Aerospace Structures, Delft University of Technology, Delft, The Netherlands, Dec. 2005.

Blom, "Optimization of course locations in fiber-placed panels for general fiber angle distributions," Composites Science and Technology, 2010.

Lozano "A review on design for manufacture of variable stiffness composite laminates." Proceedings of the Institution of Mechanical engineers, Part B: Journal of Engineering Manufacture, 2016.

Brooks, "High-fidelity Aerostructural Optimization of a High Aspect Ratio Tow-steered Wing," 57th AIAA/ASCE/AHS/ASC Structures, Structural Dynamics, and Materials Conference, AIAA SciTech, 2016.

CGTech Vericut, "Vericut composite paths for engineering," brochure, 2016.

Silva, "Composite Design," 3ds. http://www.3ds.com/fileadmin/PRODUCTS/SIMULIA/PDF/scc-papers/2015/scc2015-howsimulia-products-accelerate-dasilva.pdf, 2015.

* cited by examiner

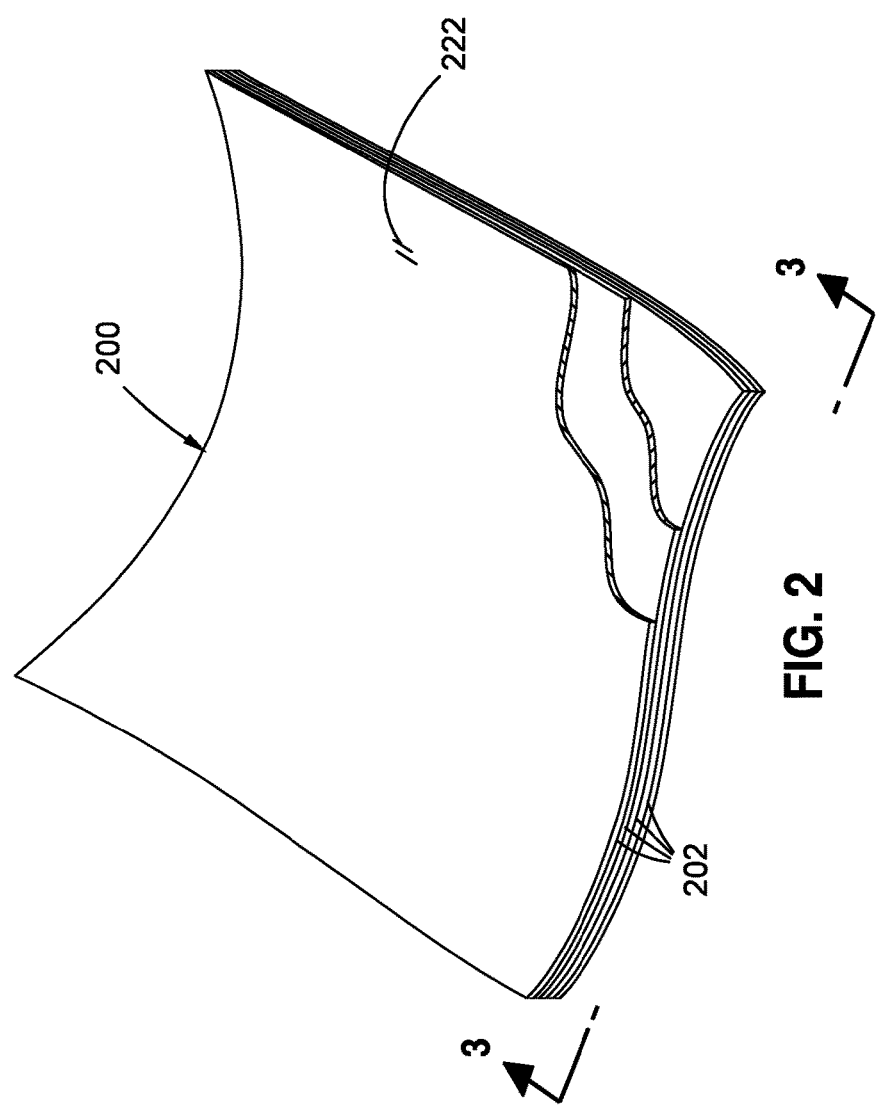
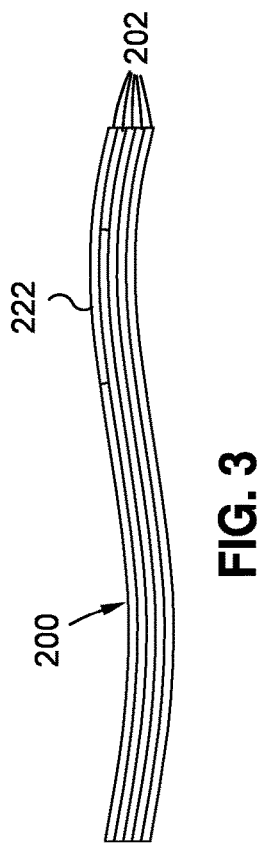

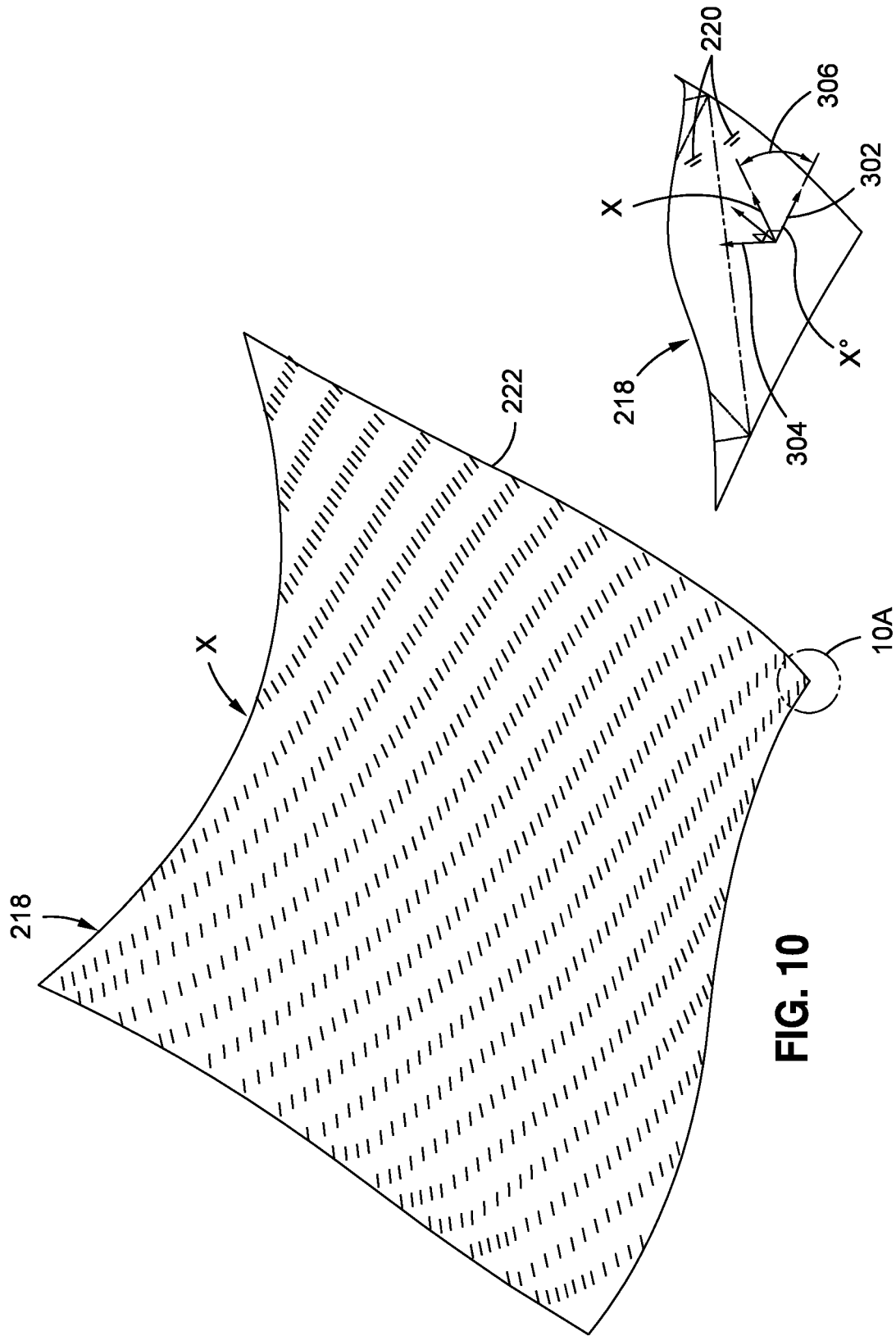

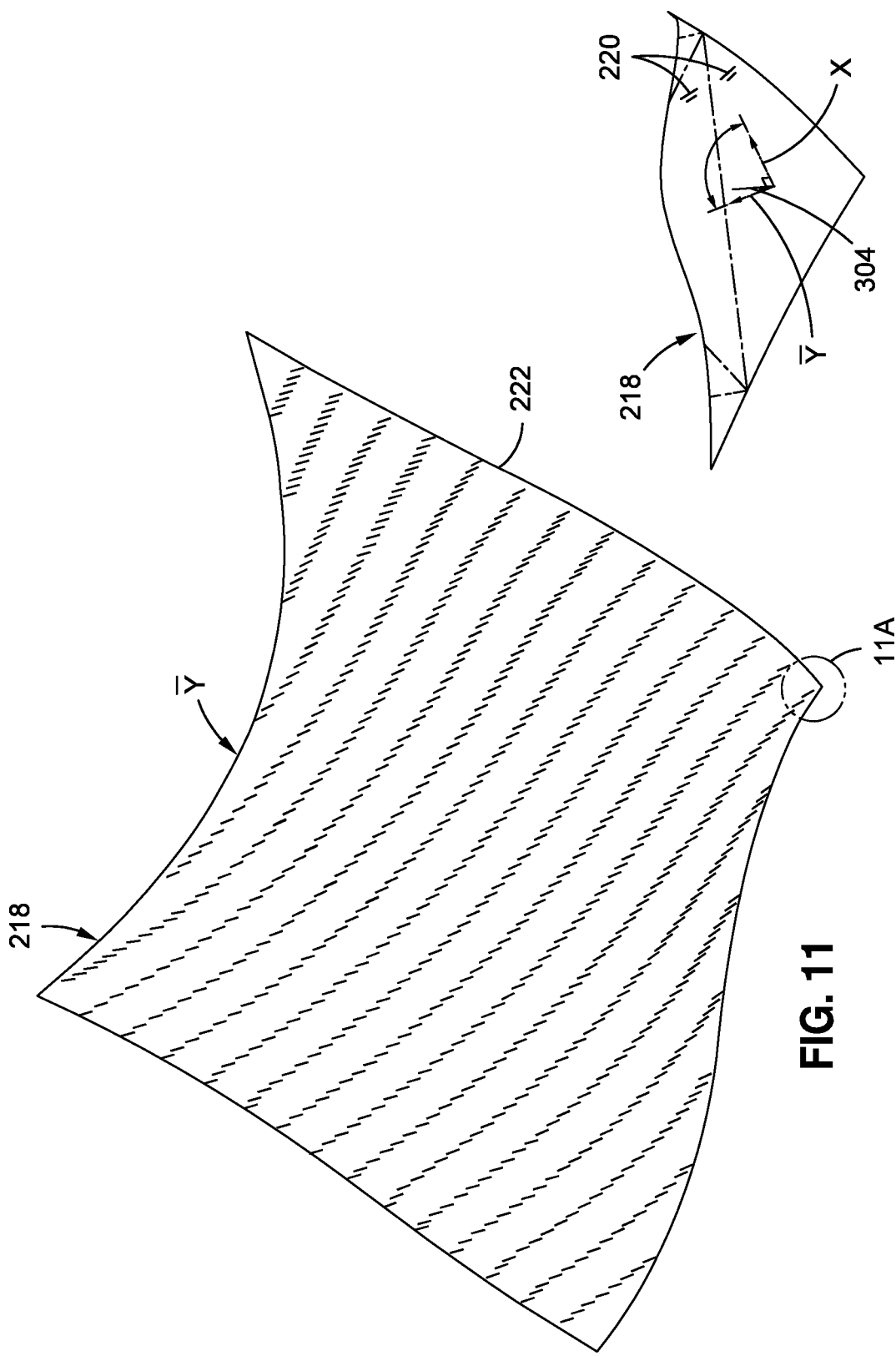

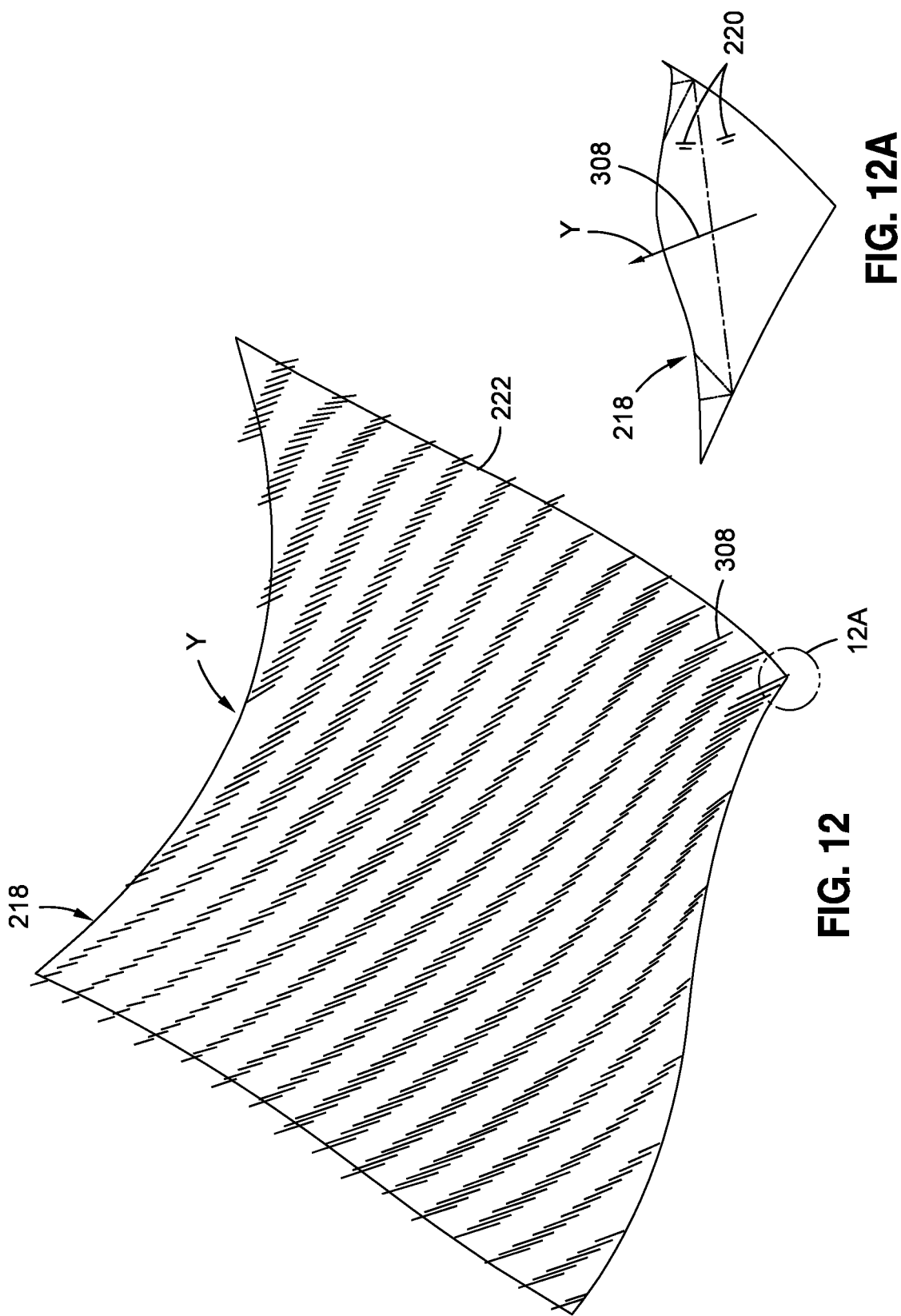

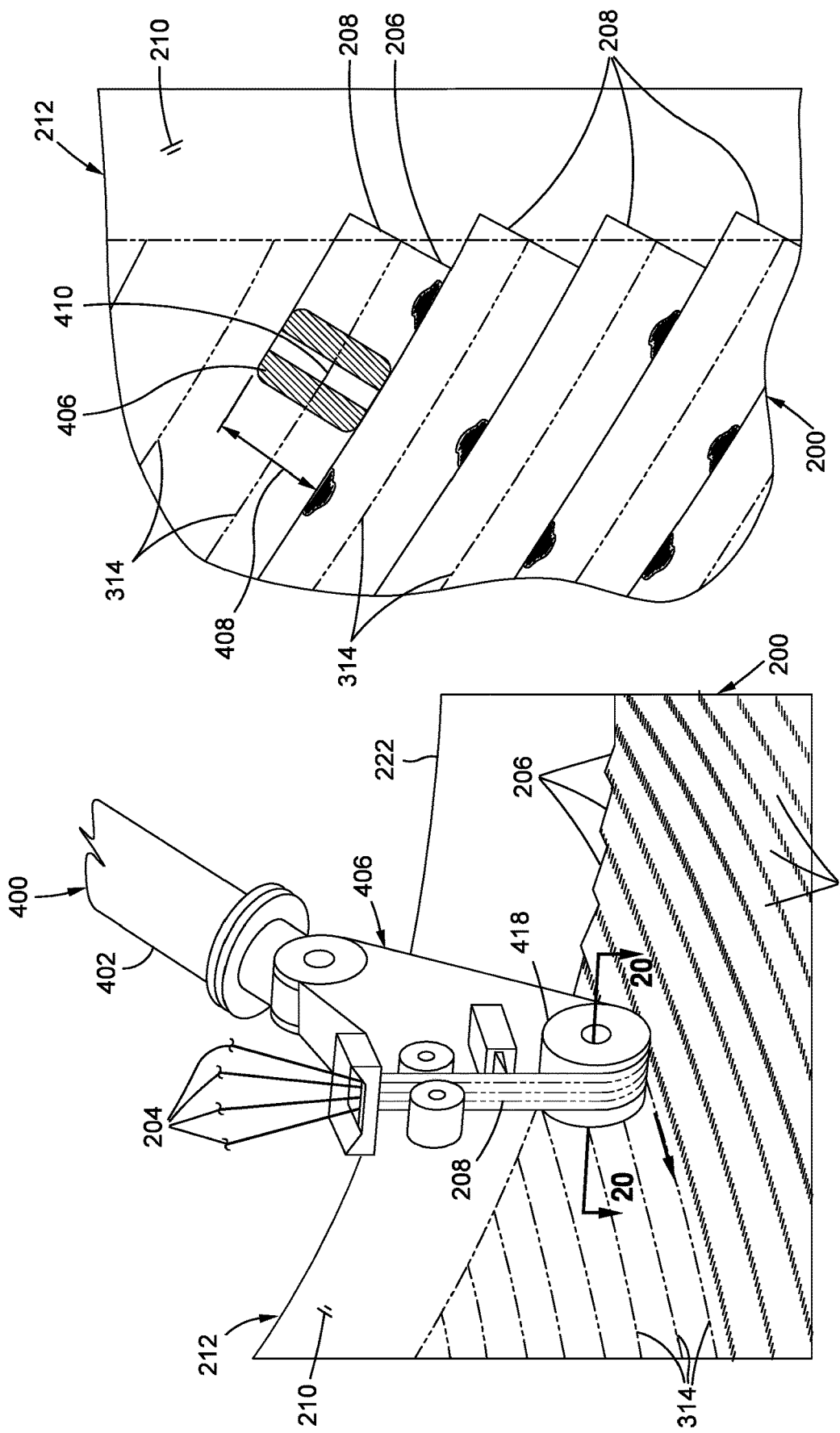

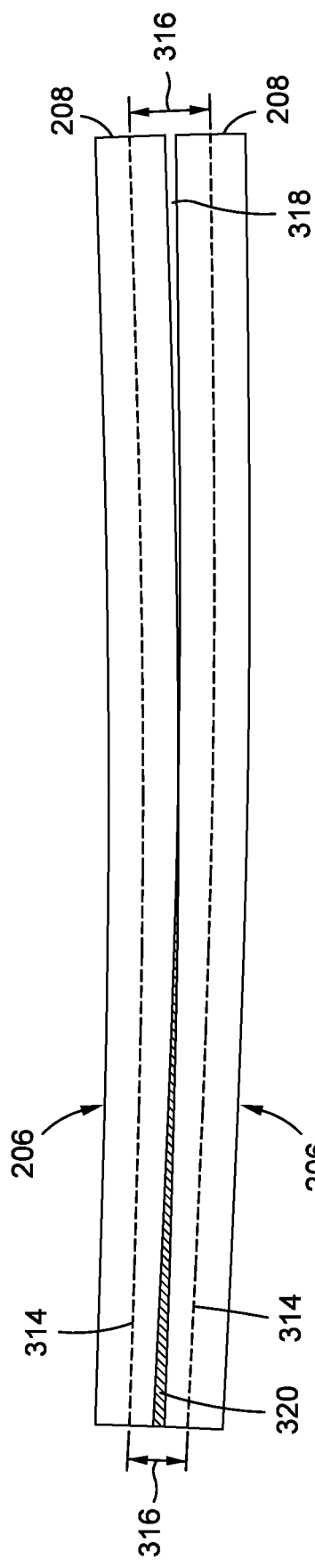
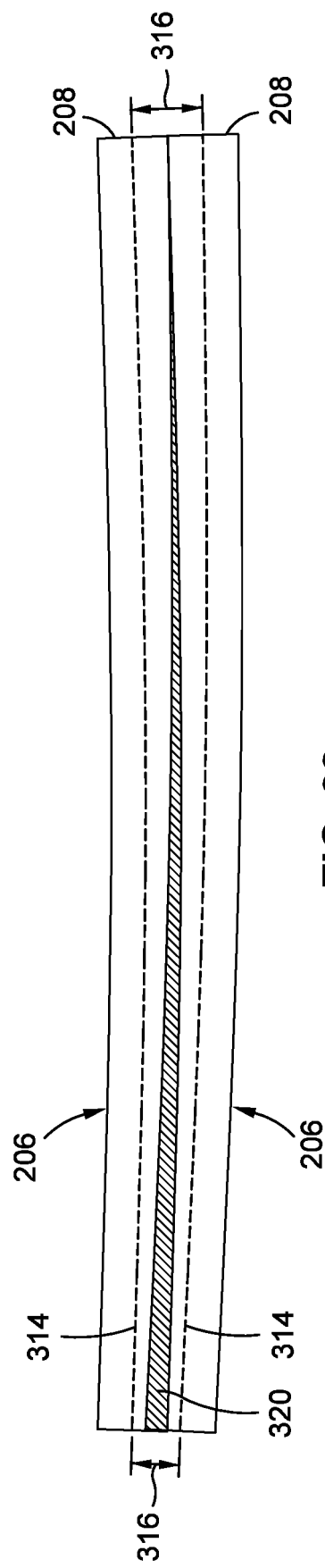

SYSTEM AND METHOD FOR DETERMINING THE DIRECTION AND SPACING OF FIBER PATHS FOR A COMPOSITE PLY

FIELD

The present disclosure relates generally to composites manufacturing and, more particularly, to a system and method for determining the direction and spacing of fiber paths for laying up composite tows to form a composite ply.

BACKGROUND

The design of a composite laminate involves specifying one or more fiber angles for each composite ply in the composite laminate. For example, a structural design engineer may specify the fiber angles of each composite ply measured relative to a reference direction on the surface of the composite ply. For visualization and for use in computational algorithms such as stress analysis software programs, the fiber angles may be represented by a vector field on the surface of the composite ply. For manufacturing the composite ply, a manufacturing engineer may model the fiber angles as continuous fiber paths when programming automated layup equipment. For example, an automated fiber placement machine (AFPM) may be programmed to lay up a plurality of variable-width courses comprising multiple composite tows along the fiber paths to form each composite ply. Each course may contain a predetermined quantity of composite tows, each of which is a continuous strip of unidirectional composite material. The AFPM may lay up a plurality of composite plies on top of each other to form a composite layup. The composite layup may be cured or hardened to form the composite laminate.

For a composite ply having a planar shape and a constant fiber angle distribution, the fiber paths are straight and parallel to each other. When a planar composite ply with constant fiber angles is laid up such as by using an AFPM, the courses may be aligned edge-to-edge with no overlaps and no gaps between adjacent courses. However, for a composite ply having a curved contour and/or a non-constant fiber angle distribution the fiber paths that follow the fiber directions specified in the fiber angle distribution may not be parallel to each other. As a result, the courses may converge and/or diverge at certain locations on the composite ply, causing overlaps and/or gaps between adjacent courses. The overlaps and gaps may negatively impact the structural properties (e.g., strength, stiffness), surface quality, and manufacturability of the composite laminate. Furthermore, the inability of design engineers to consider the effects of convergence and divergence on the manufacturability of a composite laminate may lead to expensive and time-consuming rework of the composite laminate during manufacturing. In addition, the inability to consider convergence and divergence during the design stage of a composite laminate may mean that more efficient designs are never considered.

As can be seen, there exists a need in the art for a system and method for determining fiber paths that match the fiber angle distribution specified for a composite ply and which allows for optimizing the spacing of the fiber paths by quantifying the convergence and/or divergence of such fiber paths.

SUMMARY

The above-noted needs associated with determining fibers paths are specifically addressed and alleviated by the present disclosure which provides a method of determining a direction and spacing of fibers paths for a composite ply of a composite layup given a surface definition and a fiber angle definition having one or more fiber angles. The method includes generating a surface approximation of the surface definition comprising a triangulated surface having a mesh of triangles. The composite ply has at least one of the following characteristics: the surface definition has a non-planar contour, the fiber angle definition comprises non-constant fiber angles. The method includes defining on the triangulated surface a first unit vector field establishing a 0-degree direction for each one of the triangles, wherein the 0-degree direction is the direction from which the one or more fiber angles are measured. Furthermore, the method includes defining on the triangulated surface a second unit vector field by rotating, through the one or more fiber angles specified in the fiber angle definition, the first unit vector field about surface normals respectively corresponding to the triangles. The method also includes defining on the triangulated surface a third unit vector field representing the direction of the gradient of a potential function, by rotating the second unit vector field 90° about the respective surface normals.

The method further includes determining a magnitude function to scale the third unit vector field over the triangulated surface to create a non-unit vector field to enable fitting the potential function to the second unit vector field, by minimizing the curl of the non-unit vector field. Additionally, the method includes determining the potential function having contour lines, wherein the potential function is a first potential function that is determined by performing a least-squares fit such that the direction and magnitude of the gradient of the first potential function best approximate the direction and the magnitude function of the non-unit vector field. The method also includes performing a normalization of the potential function by applying a scaling function to the potential function such that the contour lines are uniformly distributed across the triangulated surface. In addition, the method includes using the contour lines of the normalized potential function as fiber paths for fabricating the composite ply by laying up courses of composite tape along the fiber paths. For example, the method includes using the contour lines as fiber paths in a layup program that is used by an automated fiber placement machine for laying up the courses of composite tape.

Also disclosed is a processor-based system for determining a direction and spacing of fiber paths for a composite ply of a composite layup given a surface definition of the composite ply and a fiber angle definition having one or more fiber angles. The processor-based system includes a surface approximator configured to generate a surface approximation of the composite ply comprising a triangulated surface including a mesh of triangles representing the surface definition. As mentioned above, the composite ply has at least one of the following characteristics: the surface definition has a non-planar contour, the fiber angle definition comprises non-constant fiber angles. The processor-based system also includes a vector field definer configured to define on the triangulated surface a first unit vector field establishing a 0-degree direction for each one of the triangles, the 0-degree direction being the direction from which the one or more fiber angles are measured. The vector field definer is additionally configured to define on the triangulated surface a second unit vector field by rotating, through the one or more fiber angles specified in the fiber angle definition, the first unit vector field about surface normals respectively corresponding to the triangles. The vector field definer is also configured to define on the triangulated surface a third unit vector field representing a direction of a gradient of the potential function, by rotating the second unit vector field 90° about the respective surface normals.

Furthermore, the processor-based system includes a curl minimizer configured to determine a magnitude function to scale the third unit vector field over the triangulated surface to create a non-unit vector field to enable fitting the potential function to the second unit vector field, by minimizing the curl of the non-unit vector field. In addition, the processor-based system includes a potential function determiner configured to determine the potential function in the form of a first potential function by performing a least-squares fit such that the direction and magnitude of the gradient of the first potential function best approximate the direction and the magnitude function of the non-unit vector field on the triangulated surface. The processor-based system also includes a potential function normalizer configured to perform a normalization of the potential function by determining and applying a scaling function to the potential function such that the contour lines of the potential function are uniformly distributed across the triangulated surface by setting constant values of the potential function that vary at fixed intervals between adjacent pairs of contour lines. Additionally, the processor-based system includes a layup program determiner configured to use the contour lines of the normalized potential function as fiber paths in a layup program for fabricating the composite ply.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein:

FIG. 2 is a perspective view of an example of a composite laminate made up of a plurality of composite plies, each of which may be laid up by following the fibers paths determined using the presently-disclosed system and method;

FIG. 3 is a side view of the composite laminate of FIG. 2 illustrating a non-planar contour of the composite laminate;

FIG. 7A is a magnified view of a portion of the composite ply of FIG. 7 showing the orientation of fibers based on the fiber angle definition;

FIG. 10 is a perspective view of an example of a plurality of vectors of a second unit vector field defined on the triangulated surface (triangles omitted for clarity) and obtained by rotating the vectors of the first unit vector field about the triangles' surface normals over fiber angles specified by the fiber angle definition of the composite ply, and wherein the vectors of the second unit vector field represent the local fiber directions;

FIG. 10A is a magnified view of a portion of the composite ply of FIG. 10 illustrating rotation of a first unit vector on a triangle over a specified fiber angle about the surface normal of the triangle;

FIG. 11 is a perspective view of an example of a third unit vector field defined on the triangulated surface (triangles omitted for clarity) by rotating the vectors of the second unit vector field 90° about the respective surface normals of the triangles;

FIG. 11A is a magnified view of a portion of the composite ply of FIG. 11 illustrating the rotation of a second unit vector of a triangle 90° about the surface normal of the triangle;

FIG. 12 is a perspective view of an example of a plurality of vectors of a non-unit vector field defined on the triangulated surface (triangles omitted for clarity) by scaling the vectors of the third unit vector field using a magnitude function representing the magnitude of the gradient of a potential function;

FIG. 12A is a magnified view of a portion of the composite ply of FIG. 12 illustrating a non-unit vector associated with a triangle and scaled according to the magnitude function;

FIG. 19 is a magnified perspective view of the applicator head of FIG. 18 following the fibers paths while laying up courses on the layup tool;

FIG. 20 is a top view of the applicator head taken along line 20 of FIG. 19 and illustrating a centerline of the applicator head maintaining alignment with a fiber path as the applicator head lays up courses on the layup tool;

FIG. 21 is a top view of two courses partially overlapping and partially gapped relative to each other as a result of an averaging normalization of the potential function;

FIG. 22 is a top view of two courses overlapping each other with no gaps between the courses as a result of a head width normalization of the potential function;

DETAILED DESCRIPTION

Figure 1:
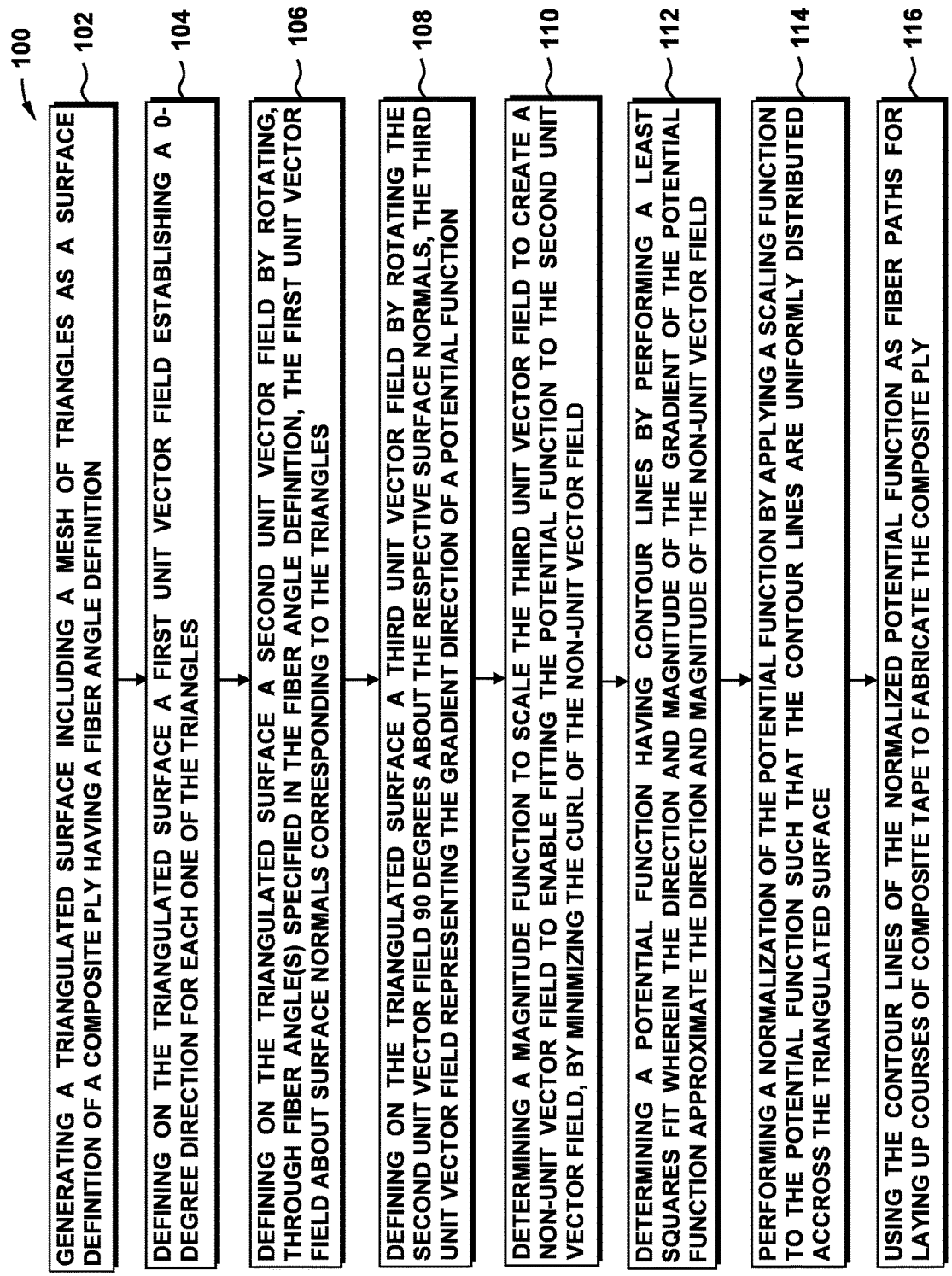
FIG. 1 illustrates a flowchart including operations of a method of determining the direction and spacing of fiber paths for a composite ply.

Referring now to the drawings wherein the showings are for purposes of illustrating preferred and various embodiments of the disclosure, shown in FIG. 1 is a flowchart of operations included in a method 100 of determining the direction and spacing 316 of fiber paths 314 (e.g., FIGS. 16 and 19-22) for laying up a composite ply 202 (FIGS. 2-3) of a composite laminate 200 (FIGS. 2-3). As described below with reference to FIGS. 2-27, the presently-disclosed method 100 and system 500 (FIG. 27) determines a potential function φ (e.g., FIGS. 13, 14, and 15) on a surface approximation (e.g., a triangulated surface 218—FIG. 8) of the composite ply 202. The potential function φ has contour lines 310 (e.g., FIGS. 13, 14, 15) that match a fiber angle definition 226 (e.g., FIGS. 4, 5, and 7) specified for the composite ply 202. After the potential function φ is determined, the potential function c is normalized by applying a scaling function to the potential function φ to uniformly distribute the contour lines 310 over the triangulated surface 218 (e.g., FIG. 8). The contour lines 310 of the normalized potential function (h°φ—FIG. 16) are used as fiber paths 314 (FIGS. 19-20) for fabricating the composite ply 202. For example, the contour lines 310 may be used in a layup program for an automated fiber placement machine 400 (AFPM—FIGS. 17-19) in which the centerline 410 (FIG. 20) of an applicator head 406 (FIGS. 18-20) of the AFPM 400 follows the fiber paths 314 when laying up courses 206 of unidirectional composite tape 208 (FIGS. 19-20) to fabricate the composite ply 202. Using the presently disclosed method 100 and system 500, the fiber paths 314 are optimized to reduce or minimize fiber path convergence or divergence occurring due to the fiber angle definition 226 (e.g., FIG. 7) specified for the composite ply 202 and/or due to the geometry (e.g., the curvature) of the surface definition 214 (e.g., FIG. 6) of the composite ply 202.

A potential function φ may be mathematically expressed as:

$$\varphi: M \to \mathbb{R} \quad \text{(Equation 100)}$$

wherein M is a surface model (not shown) of a composite ply 202 and $\mathbb{R}$ is the coordinate line. Equation 100 indicates that for any location on surface M, the potential function φ can be evaluated. As mentioned above, a fiber path 314 (e.g., FIGS. 16 and 19-20) is a contour line 310 which is a solution to the expression:

$$\varphi = c \quad \text{(Equation 101)}$$

wherein c is a constant. As described in greater detail below, the distance or spacing 316 (e.g., FIGS. 16 and 19-20) between adjacent fiber paths 314 is represented by the inverse of the magnitude of the gradient $\|\nabla\varphi\|$ of the potential function φ. A relatively large value of the magnitude of the gradient $\|\nabla\varphi\|$ corresponds to a relatively small spacing 316 between fiber paths 314, and a relatively small value of the magnitude of the gradient $\|\nabla\varphi\|$ corresponds to a relatively large spacing 316 between fiber paths 314.

FIG. 2 is a perspective view of a composite laminate 200 formed by laying up a plurality of composite plies 202 according to a predetermined stacking sequence. In some examples, each one of the composite plies 202 may have a unique fiber angle definition 226 (e.g., FIGS. 4, 5, and 7). Each one of the composite plies 202 is comprised of continuous reinforcing fibers preimpregnated with a thermoplastic matrix or a thermosetting matrix (i.e., prepreg). As shown in FIGS. 17-20 and described below, each one of the composite plies 202 may be formed by laying up courses 206 of prepreg composite tape 208 along fiber paths 314 determined by the presently-disclosed system 500 (FIG. 27) and method 100 (FIG. 1). Each course 206 of composite tape 208 may contain one or more unidirectional composite tows 204 (FIGS. 17-19) which may be provided in standard widths (e.g., 0.125, 0.25, 0.50 inch, etc.). Each composite tow may contain thousands of reinforcing filaments (not shown) which may be formed of materials such as carbon, silicon carbide, boron, ceramic, glass, and/or metallic material.

Figure 4:
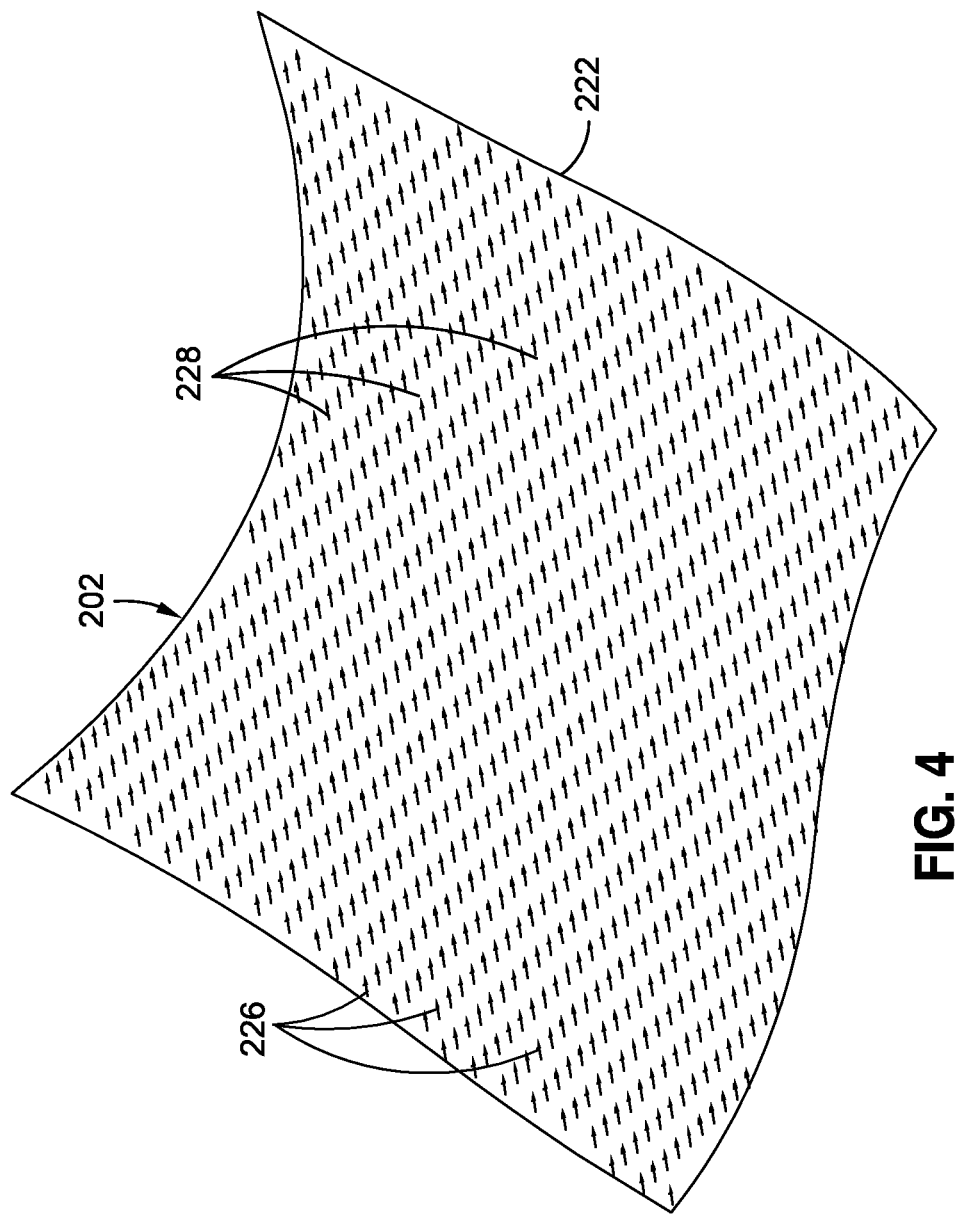
FIG. 4 is a perspective view of an example of a composite ply having a non-planar contour and constant fiber angles.
Figure 5:
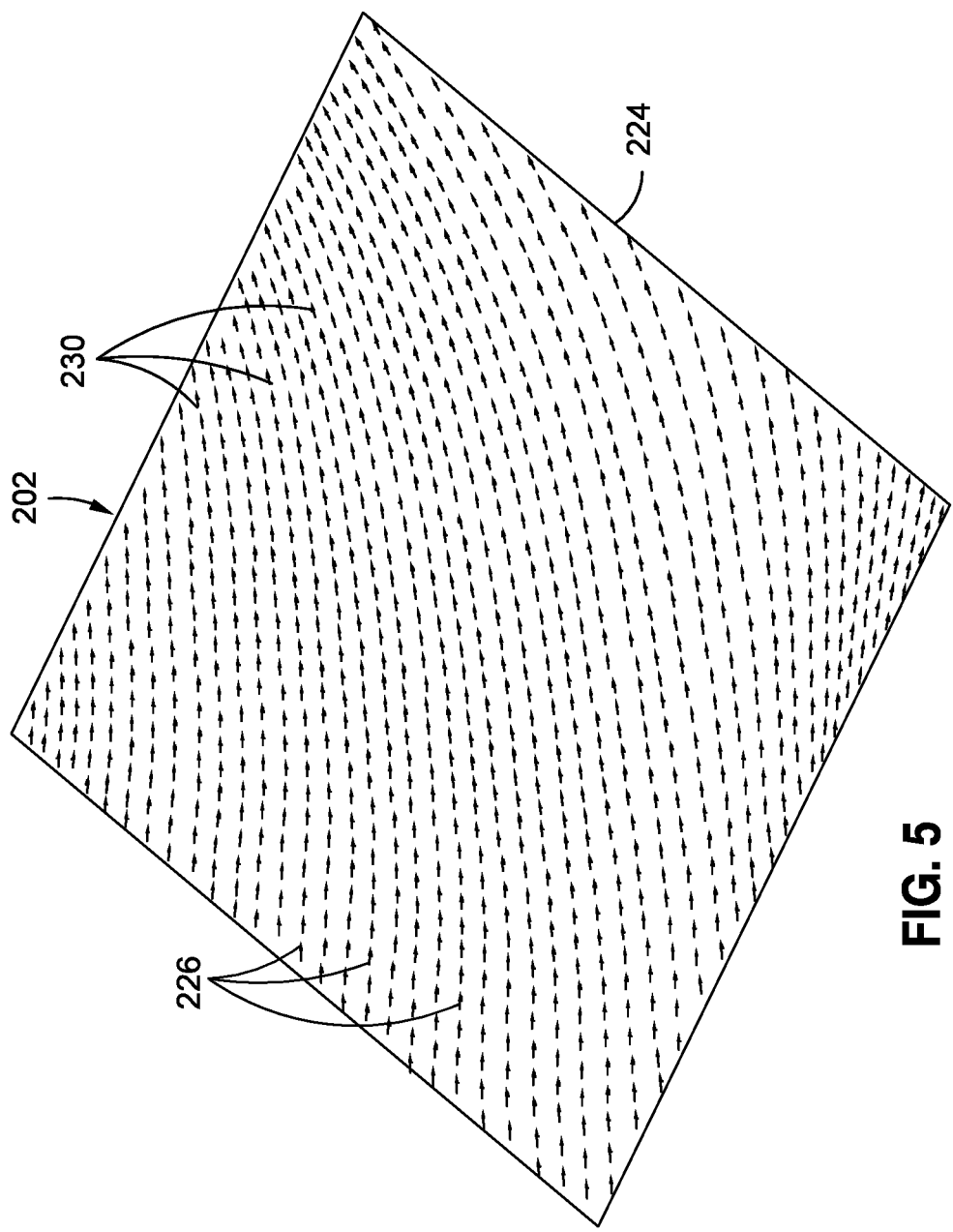
FIG. 5 is a perspective view of an example of a composite ply having a planar shape and non-constant fiber angles.

FIG. 3 is a side view of the composite laminate 200 of FIG. 2 illustrating a non-planar contour 222 of the composite laminate 200. As mentioned above, the presently-disclosed system 500 and method 100 may advantageously determine optimized fiber paths 314 (e.g., FIG. 16) given a fiber angle definition 226 (e.g., FIGS. 4, 5, and 7) for a composite ply 202 having a non-planar contour 222. For example, FIG. 4 shows a composite ply 202 having a non-planar contour 222 and a fiber angle definition 226 comprising constant fiber angles 228 for which the system 500 and method 100 may determine optimized fiber paths 314. In addition, the system 500 and method 100 may determine fiber paths 314 for a composite ply 202 having a planar shape 224 and a fiber angle definition 226 comprising non-constant fiber angles 230 as shown in FIG. 5.

Figure 6:
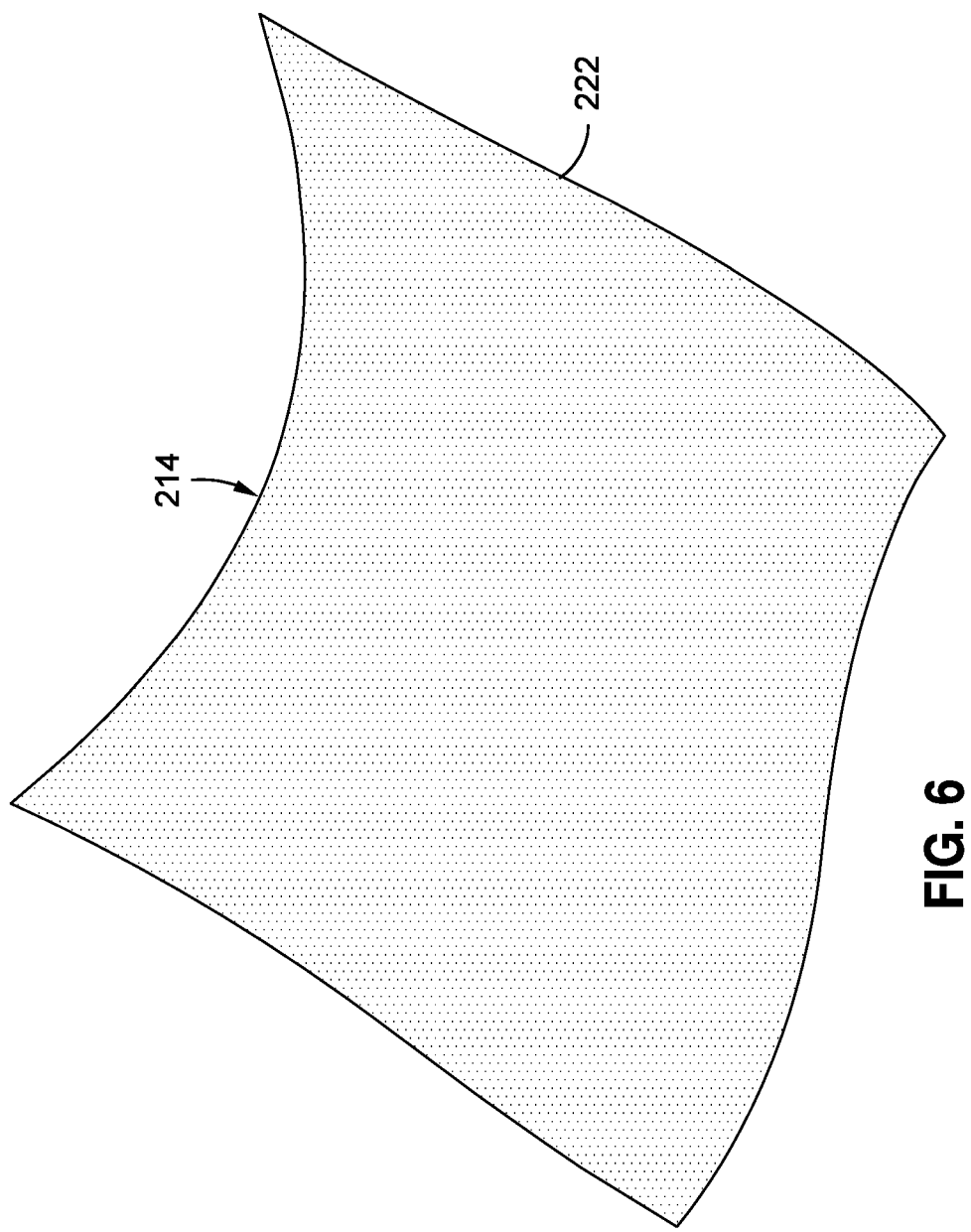
FIG. 6 is a perspective view of an example of a surface definition of a composite ply having a non-planar contour.
Figure 7:
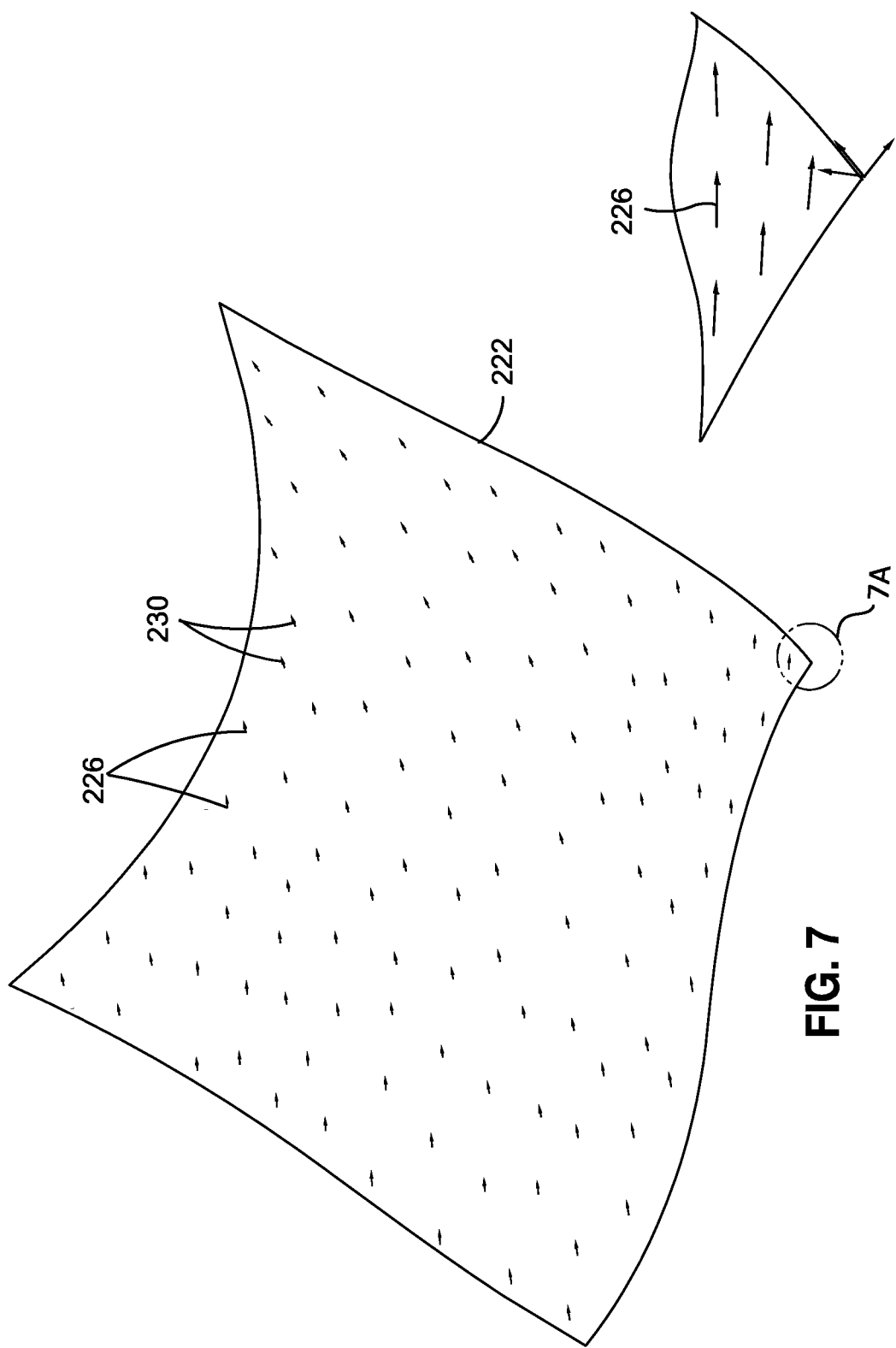
FIG. 7 is a perspective view of an example of a non-constant fiber angle definition of the composite ply of FIG. 6.

Referring to FIGS. 6-7, the presently-disclosed system 500 and method 100 is described in the context of determining fiber paths 314 for a composite ply 202 having a surface definition 214 with a non-planar contour 222 as shown in FIG. 6, and/or a fiber angle definition 226 comprising non-constant fiber angles 230 as shown in FIG. 7. FIG. 7A is a magnified view of a portion of the composite ply 202 of FIG. 7 showing the orientation of some of the fibers 230 prescribed by the fiber angle definition 226. As mentioned above, the fiber angle definition 226 for each composite ply 202 in a composite laminate 200 may be specified by a structural design engineer or a stress analyst to meet strength and stiffness requirements for a composite laminate 200.

Figure 8:
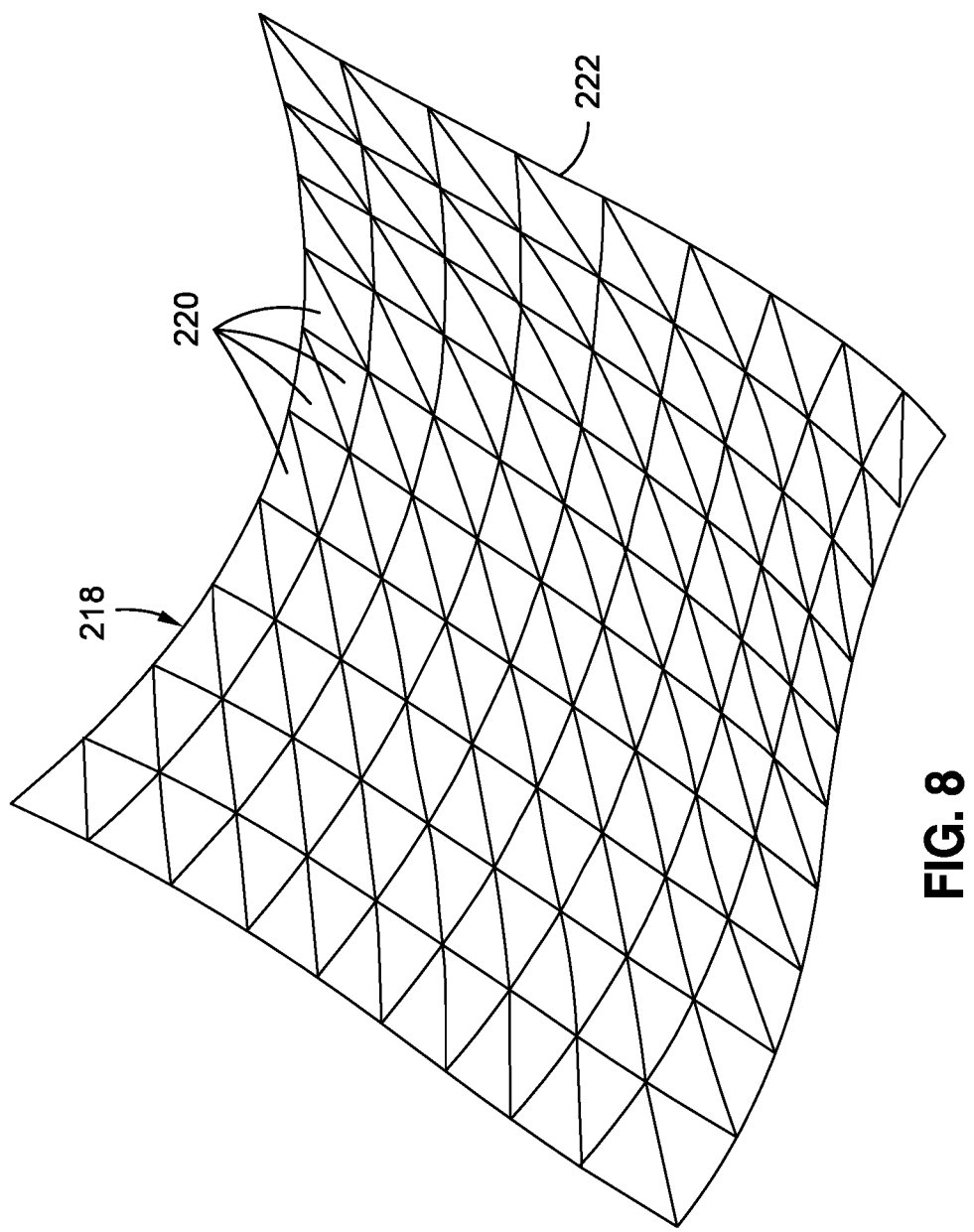
FIG. 8 is a perspective view of an example of a surface approximation of the composite ply of FIG. 6 wherein the surface approximation is a triangulated surface having a mesh of triangles and which is shown as a coarse mesh for purposes of illustration.

Referring to FIG. 8, step 102 of the method 100 (FIG. 1) includes generating a surface approximation $M_h$ of the surface definition 214 (FIG. 6) of a composite ply 202 which, in the present example, has a non-planar contour 222. The method 100 is implemented in a finite element environment in which the surface approximation $M_h$ of the composite ply 202 is a triangulated surface 218 comprised of a mesh of planar triangles 220 defining linear finite elements. The mesh size (i.e., the size of each triangle 220) is preferably small enough to capture surface features in the surface definition 214, and large enough to avoid a computationally expensive process for determining and optimizing the fiber paths 314. The triangulated surface 218 provides a computational model of the composite ply 202 that allows for the evaluation of the magnitude of the gradient of the potential function φ as a measure of the convergence and divergence of the fiber paths 314.

Figures 9, 9A:
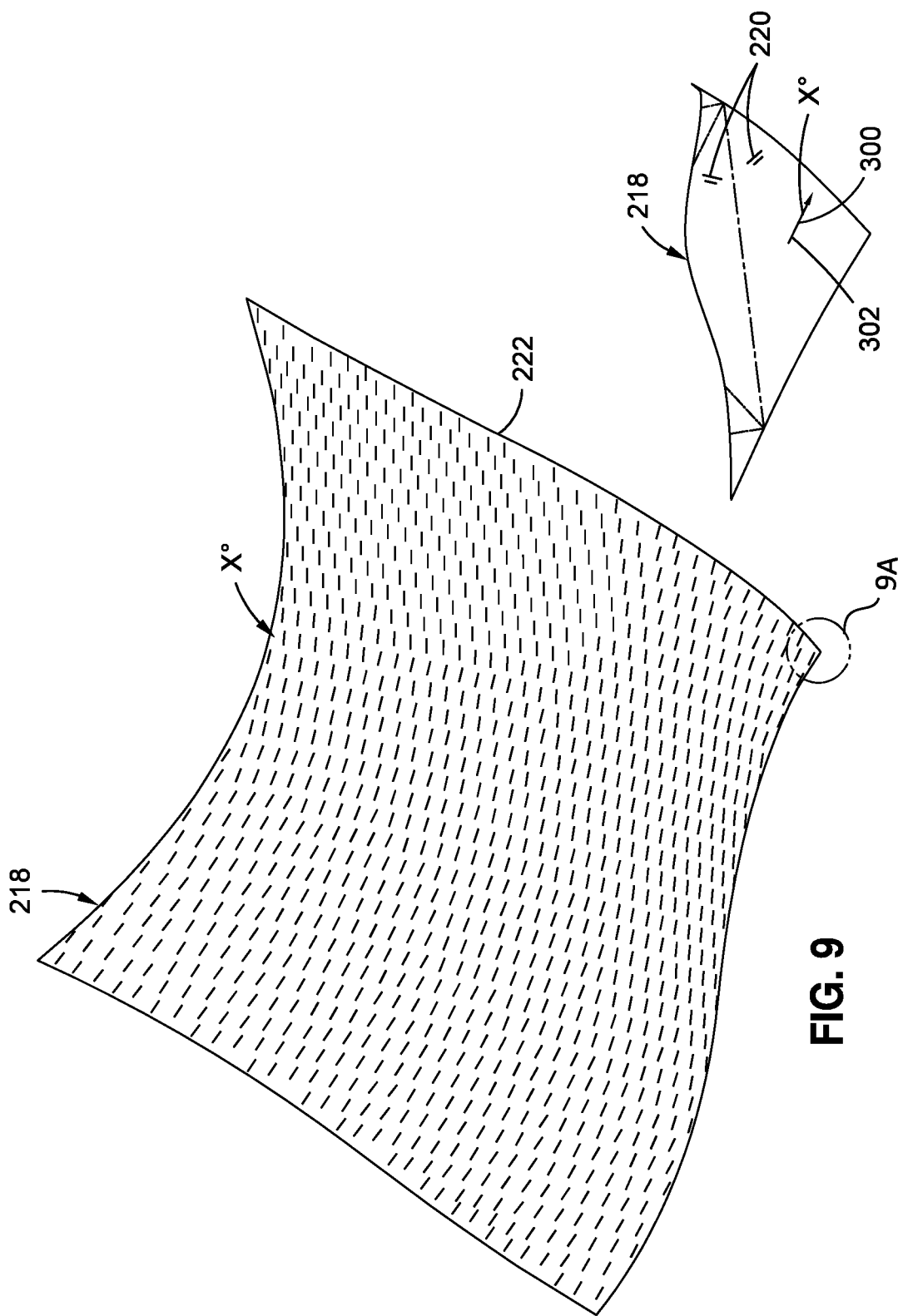
FIG. 9 is a perspective view of an example of a plurality of vectors of a first unit vector field establishing a 0-degree direction for each one of a plurality of triangles (omitted for clarity)
FIG. 9A is a magnified view of a portion of the composite ply of FIG. 9 illustrating the 0-degree direction, represented by a vector of the first unit vector field for one of the triangles.

Referring to FIG. 9, step 104 of the method 100 (FIG. 1) includes defining on the triangulated surface 218 a first unit vector field $X^0$ (i.e., a direction field) establishing a 0-degree direction 302 (FIG. 9A) for each one of the triangles 220 (FIG. 8). The first unit vector field $X^0$ serves as a composite layup reference direction and may be described as a rosette direction from which the fiber angles of the above-mentioned fiber angle definition 226 of the composite ply 202 are measured. In one embodiment, the first unit vector field $X^0$ may be defined by projecting a physical space rosette vector 300 (FIG. 9A) onto the triangulated surface 218. Alternatively, in another embodiment, the first unit vector field $X^0$ may be defined using a gradient vector field (not shown) of a potential function (not shown) defined on the surface. An example is a rectangle in the xy-plane (not shown) wherein the gradient of the x-coordinate, for example, gives a first unit vector field. In general, the coordinate functions of any parametric surface may be used in a similar manner to produce a first unit vector field. Another example would be the gradient of the height function of a cylinder (not shown) which produces the axial first unit vector field. In a still further embodiment, the first unit vector field $X^0$ may be defined by evaluating a function that describes the vector field as a function of surface coordinates. For example, the first unit vector field $X^0$ may be described by defining a function for each of the three vector components over the surface, such as $F(u,v)=\{i(u,v), j(u,v), k(u,v)\}$, wherein $F=\{i, j, k\}$ represents a vector field, and u and v are surface coordinates. If $F(u,v)$ is in the tangent space of the surface, then $X^0=F(u,v)/\|F(u,v)\|$, otherwise it is necessary to first project $F(u,v)$ onto the surface and then normalize the projection to obtain $X^0$.

Referring to FIG. 10, step 106 of the method 100 (FIG. 1) includes defining on the triangulated surface 218 a second unit vector field X by rotating the first unit vector field $X^0$ through the one or more fiber angles 306 (e.g., FIG. 7) specified in the fiber angle definition 226. The first unit vector field $X^0$ is rotated about surface normals 304 (FIG. 10A) respectively corresponding to the triangles 220 (shown in FIG. 8; omitted for clarity from FIG. 10). FIG. 10A illustrates the rotation of a first unit vector $X^0$ of a triangle 220 about the surface normal 304 of the triangle 220. The first unit vector $X^0$ is rotated through the fiber angle 306 specified (e.g., in the fiber angle definition 226) for the triangle 220. As mentioned above, the fiber angle definition 226 for a composite ply 202 may comprise constant fiber angles 228 (FIG. 4—e.g., 0°, 22.5°, 30°, 45°, 90°, etc.), or the fiber angle definition 226 for a composite ply 202 may comprise non-constant fiber angles 230 (FIG. 5). In some examples, the fiber angle definition 226 for a composite ply 202 may be defined as a function of surface coordinates on the triangulated surface 218. For example, if the surface coordinates are u and v, the angle may be described as a linear function:

$$\theta(u, v) = \theta_0 + \theta_1 \frac{u}{L_u} + \theta_2 \frac{v}{L_v},$$

wherein $L_u$ and $L_v$ are characteristic lengths in the u and v directions.

Referring still to FIGS. 10-10A, the rotation of the first unit vector field $X^0$ through the fiber angles 306 specified in the fiber angle definition 226, and the conditions for determining a potential function φ that matches the fiber angles may be described mathematically as follows. Let TM be the tangent bundle of M, wherein M is the surface of the composite ply 202. TM may be described as the space of all tangent planes of M. If $X^0:M\rightarrow TM$ is a unit vector field on M, and if $\theta:M\rightarrow \mathbb{R}$ is a ply angle distribution on M, then a potential function φ corresponds to the ply angle distribution if:

$$\nabla\varphi \cdot R_{TM}(\theta)X^0=0 \quad \text{(Equation 102)}$$

wherein $R_{TM}(\theta):M\rightarrow SO(3)$ is the rotation through θ in the tangent bundle of M and SO(3) is the space of rotation matrices in three dimensional coordinate space. Solutions to Equation 102 exist if M, θ, and $(R_{TM}(\theta)X^0)^\perp$ are smooth and $X^0$ is non-vanishing. For a given unit vector field $X^0$ and ply angle distribution θ, there may be many potential functions φ that solve Equation 102. Different potential functions φ have different gradient magnitude functions, each of which has varying degrees of manufacturability with regard to the amount of convergence and divergence associated with the gradient magnitude function. Given a potential function φ solution to Equation 102 and considering h∈$C^\infty$ you, a smooth function, the composition h∘φ is also a solution considering that:

$$\nabla(h\circ\varphi)=h'(\varphi)\nabla\varphi \quad \text{(Equation 103)}$$

by the chain rule as known in the art. In Equation 103, h effectively scales the gradients along a contour line 310 at c by h'(c). If the sets $\varphi^{-1}(c)$ are connected, then solutions to Equation 102 with non-vanishing gradient are unique up to composition with potential functions φ in $C^\infty$ and additive constants. Modeling potential functions for manufacturability requires: (1) fitting a potential function φ to the unit vector field $Y=(R_{TM}(\theta)X^0)^\perp$, and (2) finding a scaling function h that produces a desirable gradient magnitude function.

Referring to FIG. 11, step 108 of the method 100 (FIG. 1) includes defining on the triangulated surface 218 a third unit vector field $\overline{Y}$ representing a direction of a gradient $\nabla\varphi$ of the potential function φ, by rotating the second unit vector field X over 90° about the respective surface normals 304 of the triangulated surface 218 (triangles omitted for clarity from FIG. 11). The direction of the gradient $\nabla\varphi$ represents the direction along which the spacing 316 of the contour lines 310 is measured. FIG. 11A shows the rotation of a second unit vector X over 90° about a surface normal 304 of the triangle 220. The third unit vector field $\overline{Y}$ may be mathematically defined as $\overline{Y}=(R_{TM}(\theta)X^0)^\perp=X^\perp$.

Referring to FIG. 12, step 110 of the method 100 (FIG. 1) includes determining a magnitude function $f$ to scale the third unit vector field $\overline{Y}$ over the triangulated surface 218 (triangles omitted for clarity from FIG. 12). The scaling of the third unit vector field $\overline{Y}$ via the magnitude function $f$ results in a non-unit vector field Y enabling the fitting of the directions of the contour lines 310 of the potential function φ to the second unit vector field X, by minimizing the curl of the non-unit vector field Y. FIG. 12A shows a non-unit vector Y scaled according to the magnitude function $f$. In FIG. 12, each vector in the non-unit vector field Y is scaled to a magnitude that corresponds to the magnitude of the gradient 308 (i.e., rate of change) of the potential function φ. The longer the non-unit vector Y, the smaller the spacing 316 (FIG. 13) between contour lines 310 (FIG. 13) and the larger the gradient 308 of the potential function φ. The non-unit vector field Y is a first approximation of the spacing 316 (FIG. 16) between adjacent contour lines 310 of the potential function φ. As described in greater detail below, the contour lines 310 are ultimately used as fiber paths 314 along which unidirectional composite tows 204 (FIGS. 17-19) are laid up to form a composite ply 202. The inverse of the gradient magnitude represents the spacing 316 between contour lines 310. The change in the magnitude of the gradient 308 along the direction of a contour line 310 indicates convergence if the gradient magnitude increases, or divergence if the gradient magnitude decreases. The change in gradient magnitude is affected both by the fiber angles specified in the fiber angle definition 226 (e.g., FIGS. 4, 5, and 7) and by the surface contour (e.g., the amount of surface curvature) of the surface definition 214 (FIG. 6) of the composite ply 202.

Mathematically, the process of determining a magnitude function $f$ to scale the third unit vector field $\overline{Y}$ may be described using the fact that on a simply connected surface M, a vector field is the gradient of a potential function if and only if the curl of the vector field vanishes. For a discrete vector field, the result is analogous. Defining some terminology, a discrete vector field Y on a triangulated surface approximation $M_h$ with n triangles comprises a tuple of vectors: $Y=(Y_0, \ldots, Y_{n-1})$ where $Y_j$ is a vector in the plane defined by the triangle $t_j$. For a triangulated surface 218 having triangles $t_i$ and $t_j$ (not shown) with a common edge e oriented positively in $t_i$, define:

$$rot_h{}^*Y(e) = Y_j \cdot e - Y_i \cdot e \qquad \text{(Equation 104)}$$

On a simply connected triangulated surface $M_h$ (e.g., the surface approximation $M_h$ in FIG. 9 containing no disconnected surface pieces and no holes), Y is the gradient of a potential function if and only if $rot_h{}^*Y(e)=0$ for all interior edges e. Equation 104 may be rewritten in terms of sparse matrix multiplication. For example, let the number of interior edges in a surface approximation $M_h$ be p, let the number of triangles be n, and let E be the p-by-3n matrix consisting of 1×3 blocks with the (i, j)-th block equal to plus/minus the i-th interior edge if that edge is adjacent to the j-th triangle 220, and is negatively/positively oriented in that triangle 220, and zero otherwise. In terms of the sparse matrix E, Equation 104 can be restated as follows:

$$EY=0 \qquad \text{(Equation 105)}$$

In Equation 105, the discrete vector field is thought of as a 3n-by-1 column matrix. Let $I_Y$ be the 3n-by-n matrix whose (3j+k, j) entry is $(Y_j)_k$ for $k \in \{0, 1, 2\}$ (the k-th coordinate of the j-th vector of Y), and otherwise is zero. A vector field that is the gradient of a potential function and that is in the direction of the non-vanishing vector field Y can be constructed from a coordinate-wise positive solution to:

$$EI_Y f = 0 \qquad \text{(Equation 106)}$$

wherein $f$ is a column vector representing a member in the set $\overline{S}_h$ that contains all functions $\eta: M \to \mathbb{R}$ that are constant on each triangle of $M_h$. Solutions to Equation 106 are elements of the nullspace of $EI_Y$. However, there need not be a coordinate-wise positive vector in the nullspace. Instead, Equation 106 can be restated as an optimization problem as follows:

$$\min_f \|EI_Y f\|^2 \qquad \text{(Equation 107)}$$

subject to: $f>0$. If Y is an approximation to a continuous non-vanishing vector field on a compact surface M, then the open lower bound constraint can be replaced with $0<\varepsilon \leq f$ which is a convex optimization problem on a convex domain. It has been observed that the objective function can be quite flat near an optimum, to the extent that even with very tight tolerances, it is not possible to extract good scaling functions $f$ from Equation 107. If the $l_\infty$ norm is used, the problem can be restated as the following sparse linear program:

$$\min_{f,t} t \qquad \text{(Equation 108)}$$

subject to: $EI_Y f \leq t\mathbf{1}$, $EI_Y f \geq -t\mathbf{1}$, $f \geq \varepsilon$, $t \geq 0$, wherein 1 is a column vector of all ones. The dual-simplex method can be used to solve Equation 108 with overall good results.

Figure 13:
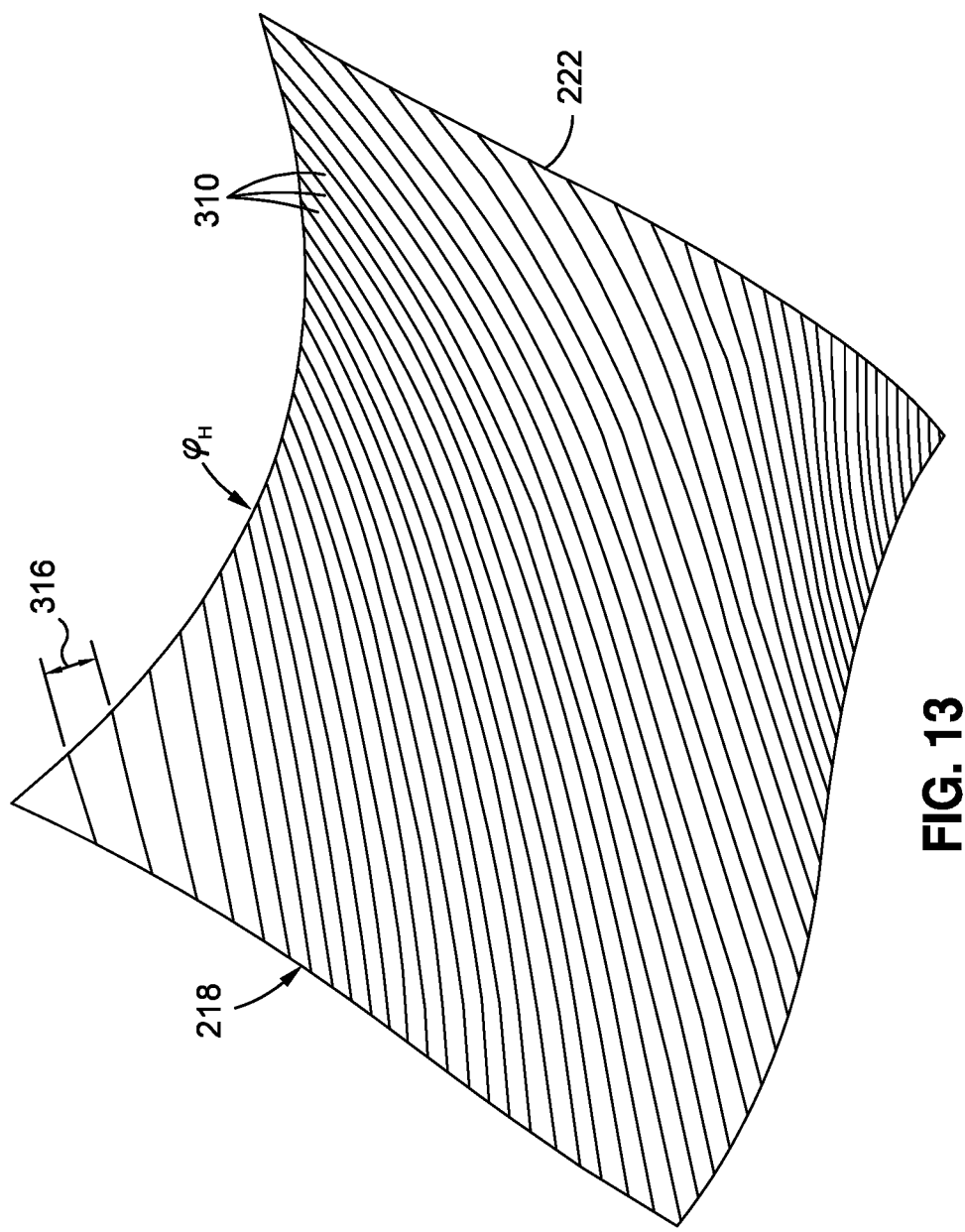
FIG. 13 is a perspective view of an example of a first potential function of the composite ply having contour lines representing fiber paths approximating the fiber angle distribution corresponding to the second unit vector field.

Referring to FIG. 13, step 112 of the method 100 (FIG. 1) includes determining a potential function φ that matches the fiber angles specified in the fiber angle definition 226, and also results in favorable fiber path spacing 316 with regard to the effect of fiber path convergence and divergence on manufacturability and other considerations such as strength and stiffness. FIG. 13 is a perspective view of a first potential function $\varphi_H$ of the composite ply 202 having contour lines 310 representing fiber paths 314 approximating the fiber angle distribution corresponding to the second unit vector field X. The first potential function $\varphi_H$ is determined by finding a least-squares fit such that the direction and magnitude of the gradient of the first potential function $\varphi_H$ best approximate the direction and the magnitude function $f$ of the non-unit vector field Y. In this regard, the first potential function $\varphi_H$ has a gradient that is the best possible least squares fit to the magnitude function $f$ and direction of the non-unit vector field Y.

The process of finding the least-squares fit may be performed using the Helmholtz-Hodge Decomposition (HHD) with the goal of finding a potential function $\varphi \in S_h$ (i.e., the first potential function $\varphi_H$) such that the gradient of the potential function φ has approximately the same direction as a vector field Y (e.g., FIG. 12) on a surface approximation $M_h$ (e.g., FIG. 8). On $M_h$, a potential function is a member of the set $S_h$ that contains all functions $\eta: M_h \to \mathbb{R}$ that are linear on each triangle of $M_h$. A function in $S_h$ can be thought of as a tuple of numbers, one for each vertex of $M_h$, and the gradient operator of a function in $S_h$ is a linear operator defined by a matrix $\nabla$. Applying $\nabla$ to a function in $S_h$ produces a vector field on $M_h$. For this work, the relevant vector field is $Y=(R_{TM}(\theta)X^0)^\perp$ which is defined by the fiber angle definition $(R_{TM}(\theta))$ 226 relative to a rosette direction $(X^0)$, and the problem is to find a potential function φ that best captures manufacturing considerations with regard to optimizing convergence and divergence of fiber paths 314 and whose gradient is in the direction of Y. On a triangulated surface approximation $M_h$ with m vertices and n triangles, such a potential function φ can be determined by solving the following 2n-by-m system of equations:

$$\nabla \varphi = Y \qquad \text{(Equation 109)}$$

Solutions to Equation 109 are controlled by the discrete Helmholtz-Hodge Decomposition (HHD) wherein $\nabla\varphi$ is the unique rotation-free summand in the HDD of Y computed as the optimizer of the following quadratic minimization problem:

$$\min_{\varphi} \|\nabla\varphi - Y\|^2 \quad \text{(Equation 110)}$$

The solution to Equation 110 may be described as a first potential function $\varphi_H$ whose gradient approximately matches both the direction and the magnitude of the non-unit vector field Y (FIG. 12), and may result in deviations between the directions of the contour lines 310 of the potential function $\varphi_H$ and the fiber directions (e.g., X, specified by the fiber angle definition 226) relative to the laminate reference direction (represented by the first unit vector field $X^0$ for the composite ply 202). If a first potential function $\varphi_H$ determined in step 112 results in fiber angle deviations that are larger than a predetermined threshold value (e.g., greater than approximately 10°), the first potential function $\varphi_H$ may be further refined to reduce the deviation between the directions of the contour lines 310 and the directions of the fibers specified by the fiber angle definition, and/or to improve or optimize the spacing 316 between the fiber paths 314, as described in greater detail below with regard to determining a second potential function $\varphi_I$ (e.g., see FIG. 14), with possible further refinement to a third potential function $\varphi_A$ (e.g., see FIG. 15).

Figure 14:
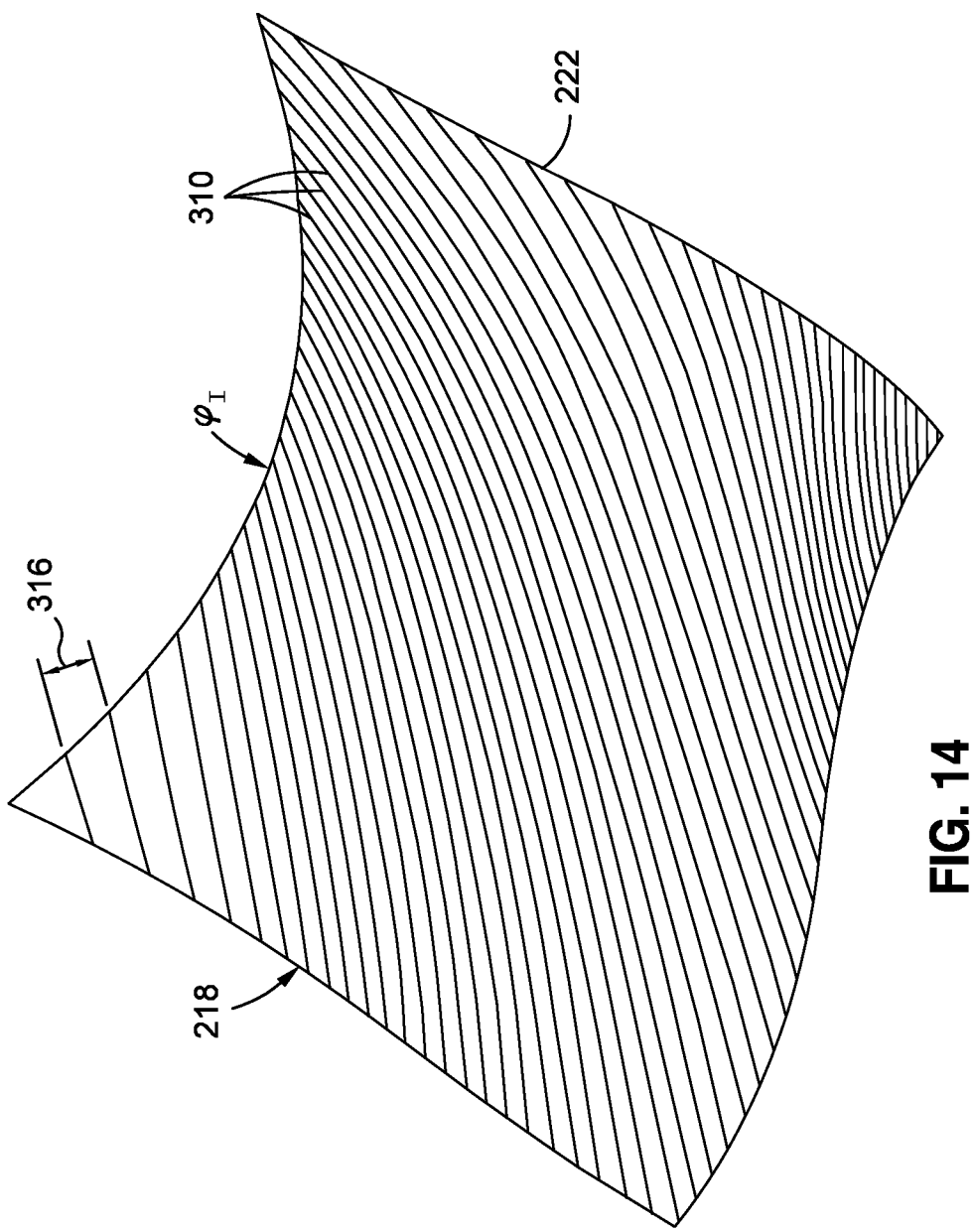
FIG. 14 is a perspective view of an example of a second potential function of the composite ply representing improved alignment of the contour lines with the second unit vector field.

Referring to FIG. 14, shown is a perspective view of a second potential function $\varphi_I$ with improved alignment of the contour lines 310 with the second unit vector field X relative to the first potential function $\varphi_H$. As mentioned above, if the first potential function $\varphi_H$ deviates from the fiber angle definition 226 by a predetermined threshold amount, the first potential function $\varphi_H$ may be refined to a second potential function $\varphi_I$ using the below-described integrating factors optimization process to improve the alignment of the contour lines 310 with the second unit vector field X. One example of deviation beyond a threshold amount may be a deviation of the orientation of the contour lines 310 from the fiber directions (i.e., the specified fiber angle definition) by more than 10° at any location along any one of the contour lines 310. In such case, the first potential function $\varphi_H$ may be refined to reduce or minimize the deviation between the direction of the non-unit vector field Y and the gradient direction of the second potential function $\varphi_I$. In addition, the refinement of the first potential function $\varphi_H$ may result in adjustment of the magnitude function for scaling the third unit vector field $\overline{Y}$ as a means to producing an overall better fit to the magnitude function and the unit vector field directions.

In the mathematical process for integrating factors optimization of the first potential function $\varphi_H$, the integrating factor for a vector field Y on a surface M is a nonzero function $u: M \to \mathbb{R}$ such that uY is the gradient of a potential function. Therefore, the desire to solve Equation 102 may be rephrased in terms of finding an integrating factor for $(R_{TM}(\theta)X)^\perp$. In this regard, a function $u: M \to \mathbb{R}$ may be sought such that $u(R_{TM}(\theta)X)^\perp$ is the gradient of a potential function. On a triangulated surface $M_h$, integrating factors lie in $\overline{S}_h$. Therefore, it is desirable to find $f \in \overline{S}_h$ such that $fY$ is the gradient of a potential function, which leads to the following optimization problem on m+n variables:

$$\min_{\varphi, f} g(\varphi, f) \quad \text{(Equation 111)}$$

subject to $f > 0$, and wherein:

$$g(\varphi, f) = \|\nabla\varphi - I_Y f\|^2 \quad \text{(Equation 112)}$$

$I_Y$ is the 3n-by-n matrix whose (3j+k, j) entry is $(Y_j)_k$ for $k \in \{0, 1, 2\}$ (the k-th coordinate of the j-th vector of Y), and otherwise is zero. As in the above-described curl minimization problem (Equation 107), the positivity constraint on $f$ for Equation 111 can be replaced with a closed lower bound constraint, which results in a sparse convex optimization problem (not shown) on a convex domain. Similar to the curl minimization problem, if the $l_\infty$ norm is used, the optimization problem (Equation 111) can be restated as a sparse linear program (not shown). However, Equation 111 produces good overall results.

Figure 15:
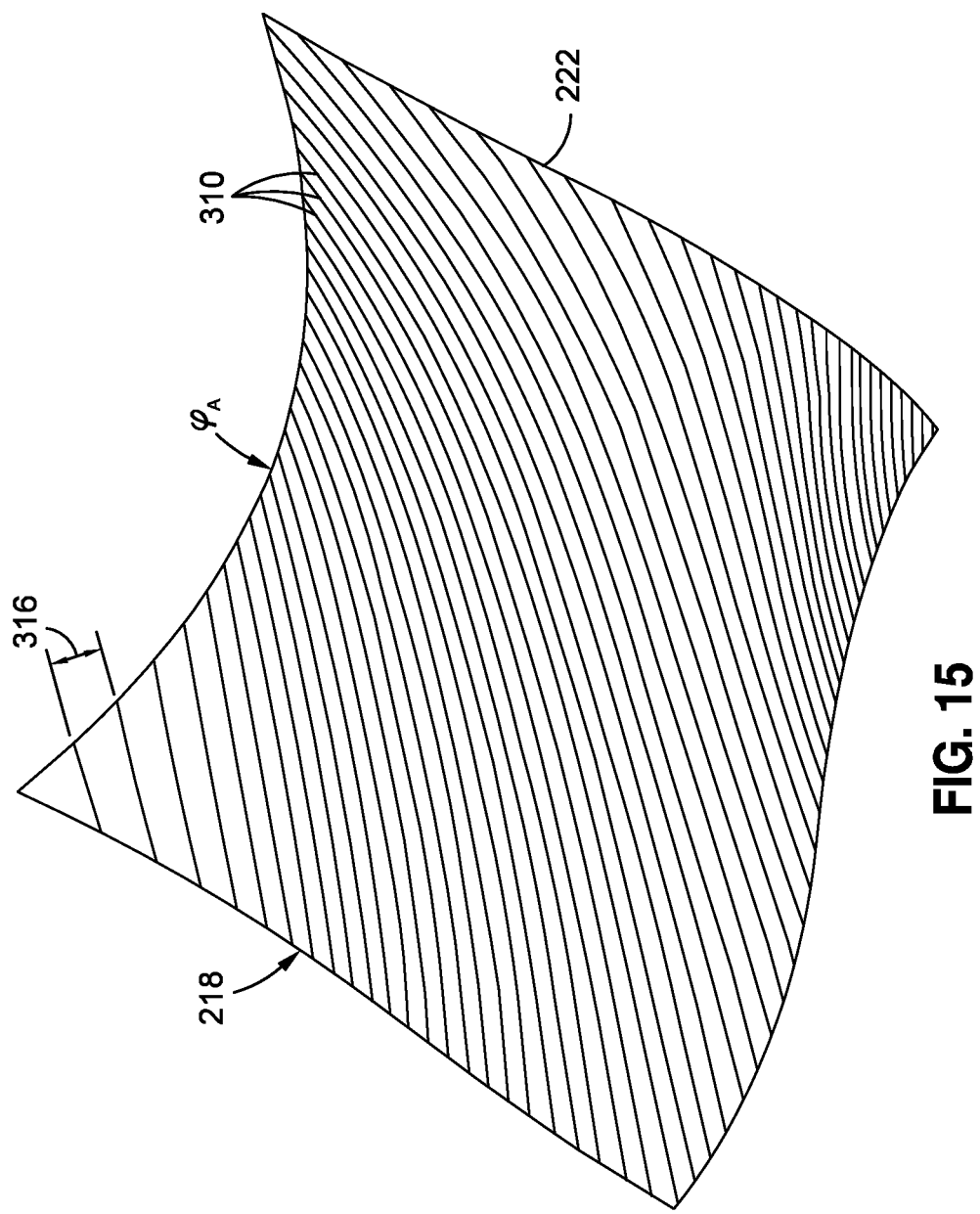
FIG. 15 is a perspective view of an example of a third potential function of the composite ply representing further improved alignment of the contour lines with the second unit vector field.

Referring to FIG. 15, shown is a perspective view of a third potential function $\varphi_A$ of the composite ply 202 representing angle optimization (i.e., improved alignment) of the contour lines 310 of the third potential function $\varphi_A$ with the second unit vector field X (FIG. 10). As indicated above, the second unit vector field X represents the fiber directions (e.g., as specified by the fiber angle definition 226) with respect to the laminate reference direction (represented by the first unit vector field $X^0$ for the composite ply 202). Performing angle optimization to produce a third potential function $\varphi_A$ involves minimizing only the deviation between the direction of the third unit vector field $\overline{Y}$ and the gradient direction of a potential function $\varphi$, and disregards the spacing 316 between the contour lines 310 (e.g., fiber paths 314) of the potential function $\varphi$. Angle optimization may be performed on the first potential function $\varphi_H$ (FIG. 13) or on the second potential function $\varphi_I$ (FIG. 14). If angle optimization is performed on the first potential function $\varphi_H$, then the above-described integrating factors optimization may optionally be performed after angle optimization.

The mathematical formulation of angle optimization involves setting up an optimization on an objective function that directly penalizes angle deviation from the third unit vector field $\overline{Y}$ (FIG. 11), and includes setting $Z = \overline{Y}^\perp$. The summands of the objective function are as follows:

$$g_{cos}(\varphi) = \sum_{j=0}^{n-1} \left( \frac{\overline{Y}_j \cdot (\nabla\varphi)_j}{\|(\nabla\varphi)_j\|} - 1 \right)^2 \quad \text{(Equation 113)}$$

and $$g_{sin}(\varphi) = \sum_{j=0}^{n-1} \left( \frac{Z_j \cdot (\nabla\varphi)_j}{\|(\nabla\varphi)_j\|} \right)^2 \quad \text{(Equation 114)}$$

If $\tau$ is a triangle-wise angle (not shown) between the third unit vector field $\overline{Y}$ and the gradient of a potential function $\varphi$, then the objective represented by Equation 113 measures the difference between the cosine of $\tau$ and one aggregated over the triangles 220 (FIG. 8), while the objective represented by Equation 114 measures the difference between the sine of $\tau$ and zero aggregated over the triangles 220. Equation 113 contains orientation information (e.g., the gradient should have the same direction as Y, not −Y) that Equation 114 lacks. However, near $\tau = 0$, Equation 113 has a horizontal tangent at each triangle 220, while Equation 114 can leverage $\sin(\tau) \approx \tau$ to produce good convergence behavior. Therefore, the optimization problem is expressed as:

$$\min_{\varphi} g_{cos}(\varphi) + g_{sin}(\varphi) \quad \text{(Equation 115)}$$

subject to $0 \leq M_- < \|(\nabla \varphi)_j\|^2 < M_+$ for all j.

Here the number of variables is m (i.e., the number of points in the triangulated surface 218). The upper bound $M_+$ is included in order to ensure that Equation 114 is not made artificially small with large gradient magnitudes.

A penalty function is introduced to avoid dealing with the above noted constraints (i.e., $0 \leq M_- < \|(\nabla \varphi)_j\|^2 < M_+$ for all j). Let $\gamma$ be the $C^2$ function defined by:

$$\gamma(x) = \begin{cases} x^3 & x > 0 \\ 0 & x \leq 0 \end{cases} \quad \text{(Equation 116)}$$

and $$g_{pen}(x_0, \ldots, x_{n-1}, a, b) = \sum_{j=0}^{n-1} \gamma(-\log(a(b - x_j))) \quad \text{(Equation 117)}$$

At $x = b - a^{-1}$, $-\log(a(b-x))$ is zero and $-\log(a(b-x))$ goes to infinity as x goes from $b-a^{-1}$ to b. Therefore, if any $x_j$ is between $b-a^{-1}$ to b, then $g_{pen}$ will be large. Composing each summand with $\gamma$ ensures that $g_{pen}$ is zero when all $x_j$ are far from b, while maintaining $C^2$ continuity.

The unconstrained optimization objective including the penalty function is:

$$g_{ang}(\varphi) = g_{cos}(\varphi) + g_{sin}(\varphi) + g_{pen}(\|(\nabla \varphi)_0\|^2, \| (\nabla \varphi)_1\|^2, \ldots, a_-, M_-) + g_{pen}(\|(\nabla \varphi)_0\|^2, \|(\nabla \varphi)_1\|^2, \ldots, a_+, M_+) \quad \text{(Equation 118)}$$

In Equation 118, $a_- < 0$, $a_+ > 0$, $M_- - a_-^{-1} < M_+ - a_+$ and the initial guess for the optimization problem $\varphi_0$ must be chosen such that $\|(\nabla \varphi_0^T)_j\|^2 \in [M_- - a_-^{-1}, M_+ - a_+]$, which can be ensured by scaling $\varphi_0$ and adjusting $M_+$. The derivative of $g_{ang}$ may be expressed analytically in terms of the following three coordinate vector fields identified as Equations 119, 120, and 121:

$$G_{cos} = \left\{ \frac{2}{\|(\nabla \varphi)_j\|} \left( \frac{Y_j \cdot (\nabla \varphi)_j}{\|(\nabla \varphi)_j\|} - 1 \right) \left( Y_j - \frac{(Y_j \cdot (\nabla \varphi)_j)(\nabla \varphi)_j}{\|(\nabla \varphi)_j\|^2} \right) \right\}_{j=0}^{n-1} \quad \text{(Equation 119)}$$

$$G_{sin} = \left\{ \frac{2 Z_j \cdot (\nabla \varphi)_j}{\|(\nabla \varphi)_j\|} (\|(\nabla \varphi)_j\|^2 Z_j - (Z_j \cdot (\nabla \varphi)_j)(\nabla \varphi)_j) \right\}_{j=0}^{n-1} \quad \text{(Equation 120)}$$

$$G_{pen}(a, b) = \left\{ 2 \frac{\partial g_{pen}}{\partial x_j} (\|(\nabla \varphi)_0\|^2, \|(\nabla \varphi)_1\|^2, \ldots, a, b)(\nabla \varphi)_j \right\}_{j=0}^{n-1} \quad \text{(Equation 121)}$$

Considering $G_{cos}$, $G_{sin}$ and $G_{pen}$ as row vectors:

$$\frac{d}{d\varphi} g_{ang} = (G_{cos} + G_{sin} + G_{pen}(a_-, M_-) + G_{pen}(a_+, M_+))\nabla \quad \text{(Equation 122)}$$

Using Equation 122, angle optimizations can be performed on a potential function $\varphi$ (e.g., either the first potential function $\varphi_H$—FIG. 13, or the second potential function $\varphi_I$—FIG. 14) to generate a third potential function $\varphi_A$ (FIG. 15) that minimizes the deviation between the orientation of the third unit vector field $\overline{Y}$ (FIG. 11) and the gradient direction of the potential function $\varphi$. Angle optimizations can be run using a quasi-Newton method. For example, angle optimizations can be run using an optimization algorithm known in the art as L-BFGS-B, and which is based on the known Broyden-Fletcher-Goldfarb-Shanno (BFGS) algorithm.

Figure 16:
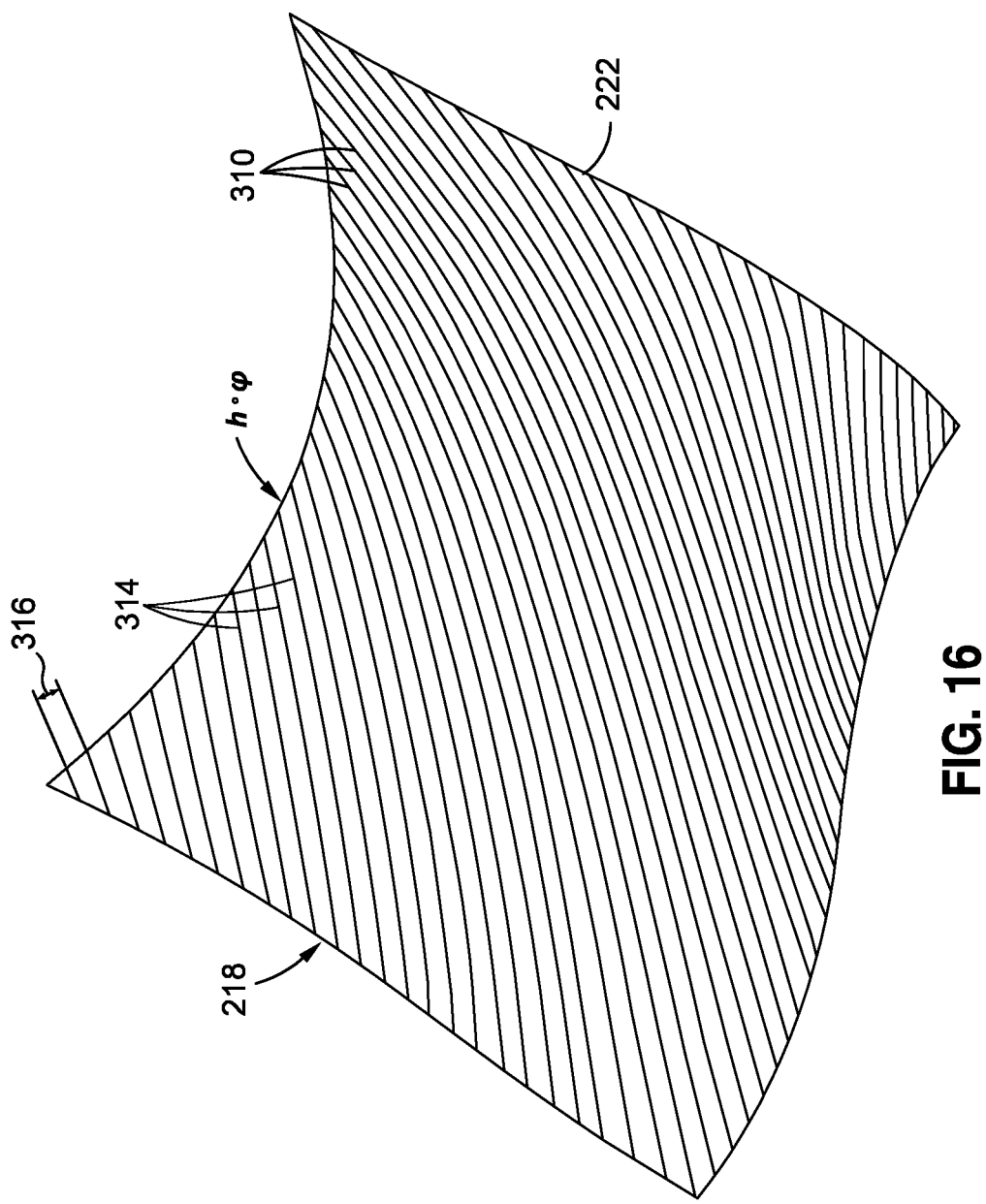
FIG. 16 is a perspective view of an example of contour lines of the composite ply after performing a normalization of the potential function in which the contour lines have a generally uniform spacing.

Referring to FIG. 16, step 114 of the method 100 (FIG. 1) includes performing a normalization of the potential function $\varphi$ (e.g., the first potential function $\varphi_H$, the second potential function $\varphi_I$, or the third potential function $\varphi_A$) after finding a potential function $\varphi$ that matches the fiber angles (e.g., FIG. 10—fiber angle definition 226) within a predetermined threshold (e.g., within 10°, within 5°, etc.). The normalization process includes applying a scaling function to the potential function $\varphi$ such that the contour lines 310 are generally uniformly redistributed across the triangulated surface 218, as shown in FIG. 16. As described below, the process of applying the scaling function includes identifying sets of triangles 220 that respectively intersect each one of the contour lines 310, and determining a distribution of the contour lines 310 by setting constant values of the potential function $\varphi$ that vary at fixed intervals between adjacent pairs of contour lines 310. An example of constant values of a potential function $\varphi$ at fixed intervals is $\varphi=1.0$, $\varphi=2.0$, $\varphi=3.0$, . . . , $\varphi=N$.

As mentioned above, for a composite ply 202 having a curved contour and/or a non-constant fiber angle distribution, the fiber paths 314 may converge and/or diverge as one moves along the fiber paths 314. During automated layup of a composite ply 202, an automated fiber placement machine 400 (AFPM—FIGS. 17-19) either lays down courses 206 of constant-width composite tape 208 which results in overlaps 320 (e.g., FIGS. 21-22) and/or gaps 318 (FIGS. 21-22) between adjacent courses 206, or the AFPM 400 has the capability of automatically changing the tape width by cutting and/or adding composite tows (FIG. 17-19) along the outer edges of the course 206 to reduce or prevent overlaps 320 and/or gaps 318 between adjacent courses 206. In Step 114, the potential function $\varphi$ is scaled in a manner to optimize the spacing 316 between contour lines 310 with values at constant intervals. In this manner, normalization of the potential function $\varphi$ results in contour lines 310 that are separated by a spacing 316 that is compatible with the head width 408 (FIG. 20) of the applicator head 406 (FIGS. 19-20) of the AFPM 400, and thereby reduces overlaps 320 and/or gaps 318 between adjacent courses 206. During the normalization process the value of the constant defining a given contour line 310 can be changed as a means to change the gradient magnitude which, in turn, changes the spacing 316 between the contour lines 310 (e.g., the fiber paths 314).

Figure 17:
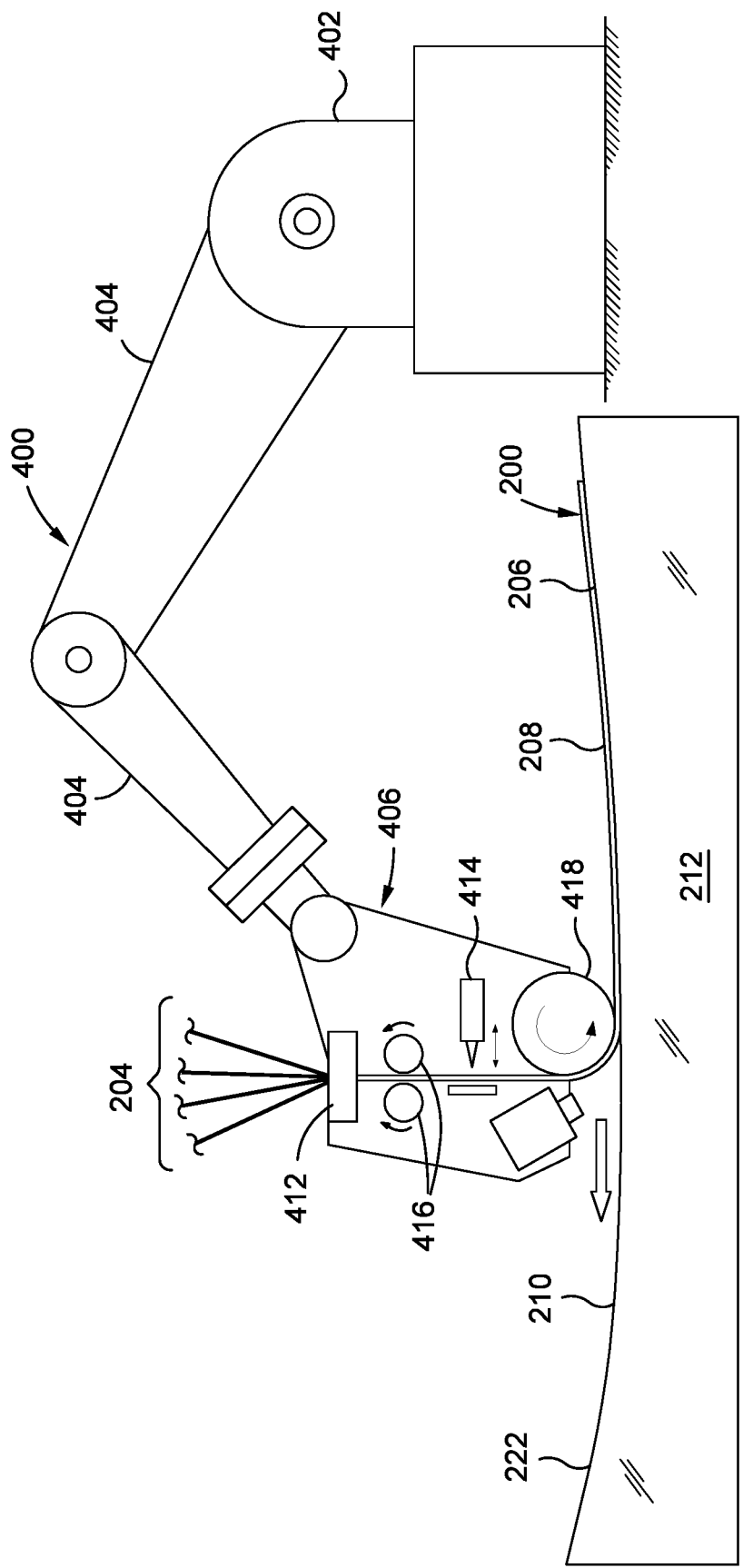
FIG. 17 is a side view of an example of an automated fiber placement machine applying a course of composite material (e.g., composite tape) onto a contoured layup tool.
Figure 18:
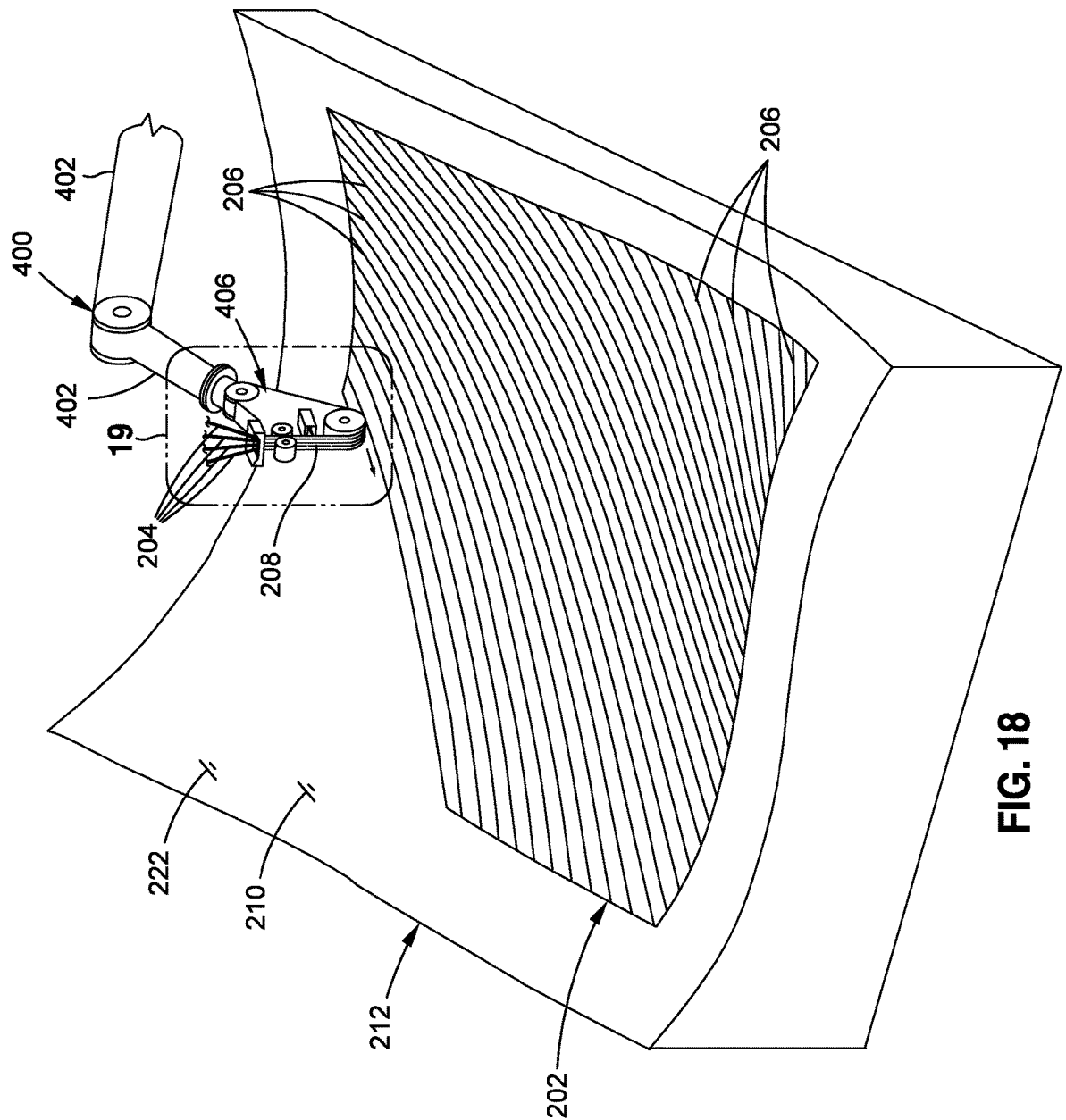
FIG. 18 is a perspective view of an example of an automated fiber placement machine laying up courses on a contoured layup tool by following the fiber paths determined by the presently-disclosed method.

In one example, normalization of a potential function $\varphi$ may be described as an averaging normalization in which a scaling function is applied to the potential function $\varphi$ to adjust the value of the potential function $\varphi$ along each contour line 310 such that the inverse of the magnitude of the gradient along each contour line 310 is, on average, equivalent to a head width 408 (FIG. 20) of an applicator head 406 of an AFPM 400 (FIGS. 17-19). In the present disclosure, the head width 408 (FIG. 20) of an AFPM 400 corresponds to the width of a course 206 of composite tape 208 to be applied by the applicator head 406 along the contour lines 310 (e.g., fiber paths 314). The width of the course 206 is the width prior to the above-mentioned optional automated adding or cutting of composite tows 204 (FIGS. 17-19) by the applicator head 406 during layup of the course 206. As described in greater detail below, the course 206 may be a composite tape 208 made up of a plurality of side-by-side composite tows (FIG. 17-19) which the applicator head 406 columnates and aligns prior to applying the composite tape 208 to a substrate 210 such as a layup tool 212 or a previously-applied composite ply 202.

Referring to FIG. 21, averaging normalization adjusts the spacing 316 between the contour lines 310 such that the average distance between two adjacent contour lines 310 is as close as possible to the head width 408 (i.e., the width of the composite tape 208 applied by the applicator head 406) and is equivalent, or as close as possible to equivalent, for each pair of contour lines 310. As mentioned above, the contour lines 310 are spaced apart at constant values of fixed intervals. The effect of averaging normalization is such that one or more pairs of adjacent courses 206 have some overlap 320 and some gaps 318 at one or more locations along the length of the pair of adjacent contour lines 310, except if a pair of adjacent courses 206 is exactly parallel to each other along their entire length, in which case no gaps 318 or overlaps 320 occur. In FIG. 21, the pair of courses 206 are overlapped along the left-hand portion, gapped along the right-hand portion, and are non-overlapping and non-gapped at an approximate mid-length location of the courses 206. In some examples, the averaging normalization of a potential function φ may be such that for each adjacent pair of courses 206, the maximum width of overlap 320 (i.e., measured perpendicular to one of the contour lines 310) at one end of the pair of courses 206 is equivalent to the maximum width of the gap 318 at an opposite end of the same pair of courses 206. In still other examples (e.g., FIG. 21), the averaging normalization of a potential function may be such that the total area of overlap 320 of a pair of courses 206 (when viewed from a top-down perspective) is equivalent to the total area of the gap 318 between the same pair of courses 206.

Referring to FIG. 22, in another example, normalization of the potential function c may be described as a head width normalization in which a scaling function is applied to the potential function φ to adjust the value of the potential function φ along each contour line 310 such that the inverse of the minimum magnitude of the gradient along each contour line 310 is not greater than the head width 408 (FIG. 20) of an applicator head 406 of an AFPM 400 (FIGS. 17-19). In this regard, head width normalization adjusts the spacing 316 between the contour lines 310 such that the maximum distance between two adjacent contour lines 310 is equivalent to the head width 408, and is the same for each pair of contour lines 310 which, as mentioned above, are spaced apart at constant values of fixed intervals. The effect of head width normalization is that the two courses 206 in each pair of adjacent courses 206 touch or overlap 320 each other along the length of the contour lines 310, with no gaps 318 between each pair of adjacent courses 206. In this regard, each pair of adjacent courses 206 exactly touch each other (without overlapping) at the location where the contour lines 310 (i.e., fiber paths 314) are furthest apart, without any gaps between each pair of adjacent courses 206. Such an arrangement ensures optimal use of the AFPM, and maximizes output, because the full width of the course can be used at the location where the contour lines 310 are furthest apart.

The mathematical formulation of normalization of a potential function φ involves finding a normalizing function $h: \mathbb{R} \to \mathbb{R}$ such that the contour lines 310 of $h \circ \varphi$ (FIG. 16) provide a model of the fiber paths 314 that is the best possible for the application at hand. In this regard, described below are two approaches, including a first approach describing the above-referenced averaging normalization (FIG. 17), followed by a second approach describing the above-referenced head width normalization (FIG. 22).

A key observation is that for any contour path φ=c on a triangulated surface approximation $M_h$ that does not pass through a node, there is a maximum length open interval $I_c = (c-\varepsilon_0, c+\varepsilon_1)$ such that for any c'∈$I_c$, the contour path φ=$c_0$ has the same simplex-wise tangent directions as φ=c. Furthermore, the upper and lower bounds of $I_c$ must be in the node-wise domain of the potential function φ, which is the finite set Φ, represented as:

$$\Phi = \{\varphi_i | 0 \le i \le m\} \quad \text{(Equation 123)}$$

If $\varphi i_0, \varphi i_1, \ldots, \varphi i_{m-1}$ is an ordering of Φ, then from the perspective of tangents and, therefore gradients, there are a finite number of contour lines 310, one for each open interval $I_k = (\varphi i_k, \varphi i_{k+1})$.

In the first approach for the averaging normalization, a generalist perspective may be taken in an attempt to produce a function h that distributes the contour lines 310 of potential function φ uniformly across the surface. Let $a_k$ be the midpoint of $I_k$ and let $T_k$ be the set of triangles 220 that intersect the contour φ=$a_k$. A uniform distribution of contour lines 310 may be obtained by making the change in the magnitude of the gradients along contour lines 310 as close to zero as possible. Therefore, it is desirable to make the magnitudes of the gradients along contour lines 310 as close to some constant as possible. Taking the constant to be one, this can be expressed for contour paths φ=c with c∈$I_k$ as the following optimization problem:

$$\min_m \sum_{t \in T_k} (m \|(\nabla \varphi)_t\| - 1)^2 \quad \text{(Equation 124)}$$

which has the solution:

$$m_k = \frac{\sum_{t \in T_k} \|(\nabla \varphi)_t\|}{\sum_{t \in T_k} \|(\nabla \varphi)_t\|^2}. \quad \text{(Equation 125)}$$

We have intervals $I_k$ such that the average of the gradient magnitudes along a contour line 310 are the same for all contour lines φ=c with c∈$I_k$, and we have numbers $m_k$ which scale those gradient magnitudes to values as close as possible to one. From this data, a piecewise linear normalizing function h can be constructed for averaging normalization of the potential function φ as shown in FIG. 21. Namely, h is the piecewise linear function with $h(\varphi_{i0})=0$, breakpoints at $\varphi i_0, \varphi i_1, \ldots, \varphi i_{m-1}$, and $h'(a_k)=k$.

Described below is the second approach for normalization of a potential function φ, and is referred to as head width normalization (FIG. 22). As mentioned above, the effect of head width normalization is that the two courses 206 in each pair of adjacent courses 206 overlap each other along the length of the contour lines 310, with at least one location along the length where the edges of the two courses 206 exactly touch each other with no gaps between each pair of adjacent courses 206. A layup program for an AFPM 400 may require that the two courses 206 in each adjacent pair are separated by no more that the head width 408 of the applicator head 406 of the AFPM 400. The approach for head width normalization models this requirement continuously by using the following slopes in the piecewise linear model described above:

$$\bar{m_k} = \frac{1}{w \, \min_{t \in T_k} \|(\nabla \varphi)_t\|} \quad \text{(Equation 126)}$$

wherein w is the head width 408 (FIG. 20) of the applicator head 406 of the AFPM 400 (FIG. 20). Equation 126 represents that the minimum gradient magnitude along a contour line 310 is set to the inverse of the head width 408 of the applicator head 406.

Referring now to FIGS. 19-22, following normalization of the potential function φ, step 116 of the method 100 (FIG. 1) includes using the contour lines 310 of the normalized potential function (h°φ, e.g., FIG. 16) as fiber paths 314 for fabricating the composite ply 202 by laying up courses 206 of composite tape 208 along the fiber paths 314. As mentioned above, in some examples, each course 206 may contain a plurality of side-by-side composite tows 204 (FIGS. 17-19) in edge-to-edge contact. However, in other examples, each course 206 may contain a single composite tow 204. The spacing 316 (i.e., at fixed intervals) between the fiber paths 314 can be selected such that the largest distance between adjacent pairs of fiber paths 314 is equivalent to the maximum width of a course 206 (e.g., composite tape 208) that is to be used to lay up a composite ply 202. If minimal or no overlap 320 of adjacent courses 206 is desired such as for structural reasons, a first estimate of the course width (e.g., composite tape width) or the quantity of composite tows 204 can be made based on the spacing 316 between adjacent fiber paths 314. If the spacing 316 between adjacent fiber paths 314 is less than the maximum course width (interchangeably referred to herein as the head width 408) that can be applied by the applicator head 406, then the course width will need to be adjusted. For example, if the spacing 316 between adjacent fiber paths 314 is half the maximum course width, then the AFPM 400 may be adjusted or programmed to apply composite tape 208 in a tape width that is half the maximum course width. The mathematical formulation for determining course width is as follows: if w is the head width 408, and wc is the course width, then it can be said that $w_c = w/\|\nabla \varphi\|$ or, in other words, $w_c \|\nabla \varphi\| = w$ which is constant along the contour line. So if the minimum value of $\|\nabla \varphi\|$ equals 1, then the course width equals the head width 408, and otherwise the course width can only be smaller. The AFPM 400 may be programmed to cut composite tows 204 along the outer edges of the courses 206 (i.e., composite tape 208) to prevent overlaps 320 between adjacent courses 206. In this regard, the method 100 may include adjusting the course width to be less than the spacing 316 between adjacent fiber paths 314 (i.e., contour lines 310) as a means to avoid overlapping of adjacent courses 206 during layup. The course width may be adjusted prior to the layup of courses 206 by initially selecting the quantity of composite tows 204 (FIG. 19) to be fed to the applicator head 406. Alternatively or additionally, the AFPM 400 may be programmed to adjust the course width by adding or cutting composite tows 204 from the side edges of the course 206 during layup to avoid overlapping of adjacent courses 206.

FIG. 17 is a side view of an example of an AFPM 400 programmed to follow the fiber paths 314 when laying up courses 206 of composite tape 208 onto a layup tool 212.

FIG. 18 is a perspective view of an AFPM 400 laying up courses 206 of composite tape 208 on a contoured layup tool 212 and illustrating the applicator head 406 following the fiber paths 314 determined by the presently-disclosed method 100. In the present disclosure, a fiber path 314 may also be referred to as a centerline path or a head path, and may be described as the path that a centerline 410 (FIG. 20) of the applicator head 406 (i.e., the centerline of a course) follows to lay down courses 206 of composite tape 208 on a substrate 210. A substrate 210 may be a layup tool 212 (e.g., FIG. 17-20), a previously laid up composite ply 202, or another type of surface. In FIGS. 19-20, the AFPM 400 may include a base 402 and one or more articulated arms 404, one of which may be rotatably coupled to the base 402. The applicator head 406 may be mounted on an end of an articulated arm 404.

It should be noted that implementation of the presently-disclosed method 100 is not limited to determining fibers paths for layup of courses 206 of composite material (e.g., composite tape 208) on stationary layup tools 212. For example, the presently-disclosed method 100 may also be implemented for layup of courses 206 on a movable layup tool (not shown) such as a rotatable mandrel. Furthermore, the presently-disclosed method 100 is not limited to implementation for an AFPM 400 having articulated arms 404, and may also be implemented for other configurations of automated layup equipment such as an overhead gantry (not shown) configured to support an applicator head 406 for laying up courses 206. In addition, the presently-disclosed method 100 may also be implemented for determining fibers paths 314 to facilitate hand layup of courses 206 by a technician instead of using an AFPM 400. For example, a technician may sequentially lay up a plurality of courses 206 of composite tapes 208 by manually aligning a centerline (not shown) of each course 206 with a corresponding fiber path 314. The fiber paths 314 may be provided (e.g., marked) on the substrate 210 using any number of means that allow a technician to visually align the centerline of each course 206 with a fiber path 314, including physically marking the fiber paths 314 directly on the substrate 210, projecting the fiber paths 314 onto the substrate 210 using an optical projection device (not shown) such as a laser beam, or by any other means. Advantageously, for hand layup of a composite ply 202 where the course 206 of composite material (e.g., composite tape 208) is laid up along a fiber path 314 as one continuous piece (i.e., not spliced), the presently-disclosed method 100 may predict the location of wrinkles (not shown) in the course 206 at regions of the composite ply 202 where convergence of fiber paths 314 is high. Alternatively, the presently-disclosed method 100 may facilitate a determination that it is not possible to lay up a course 206 along a fiber path 314 without the occurrence of wrinkles in the course 206.

FIG. 19 is a perspective view of an applicator head 406 of an AFPM 400 applying a course 206 of composite tape 208 onto a layup tool 212 to form a composite ply 202 of a composite layup. FIG. 20 is a top view of the applicator head 406 of the AFPM 400 showing the centerline 410 of the applicator head 406 being maintained in alignment with a fiber path 314 as the applicator head 406 lays up composite tape 208 on the layup tool 212. The applicator head 406 may have a collimator 412 for redirecting and aligning a plurality of composite tows 204 to form a composite tape 208, a nip 414 for cutting the composite tows 204, one or more feed rollers 416 for feeding the composite tows 204, and a compaction roller 418 for pressuring the composite tape 208 (e.g., the plurality of composite tows 204) onto a substrate 210 (e.g., a layup tool 212 surface or a previously-laid composite ply 202). The AFPM 400 may be programmed to layup a plurality of composite plies 202 on top of each other according to a predetermined stacking sequence to form a composite layup. The composite layup may be subsequently processed (e.g., vacuum bagged, degassed, consolidated, etc.) prior to curing or hardening the composite layup to form the composite laminate 200 (FIGS. 2-3).

There are some surface configurations for which potential fitting and/or normalization may fail unless additional measures are taken. One example is a circular cylinder (not shown) having fiber paths (i.e., contour lines) that are each oriented in the axial direction of the cylinder. If there is a fiber path every 30°, and the fiber path at 0° has a value of 0 and increases by 1 when going around the circumference of the cylinder, then the fiber path with value 12 will be located at 0°, where there is already a fiber path with value 0 for the potential function φ, resulting in a jump or discontinuity due to the two different values (12 and 0) at the 0° location. One solution to the cylinder example is to create one fiber path by integrating the fiber orientations over the cylindrical surface, cutting the surface along the one fiber path, and then following the above-described potential fitting steps.

Figure 23:
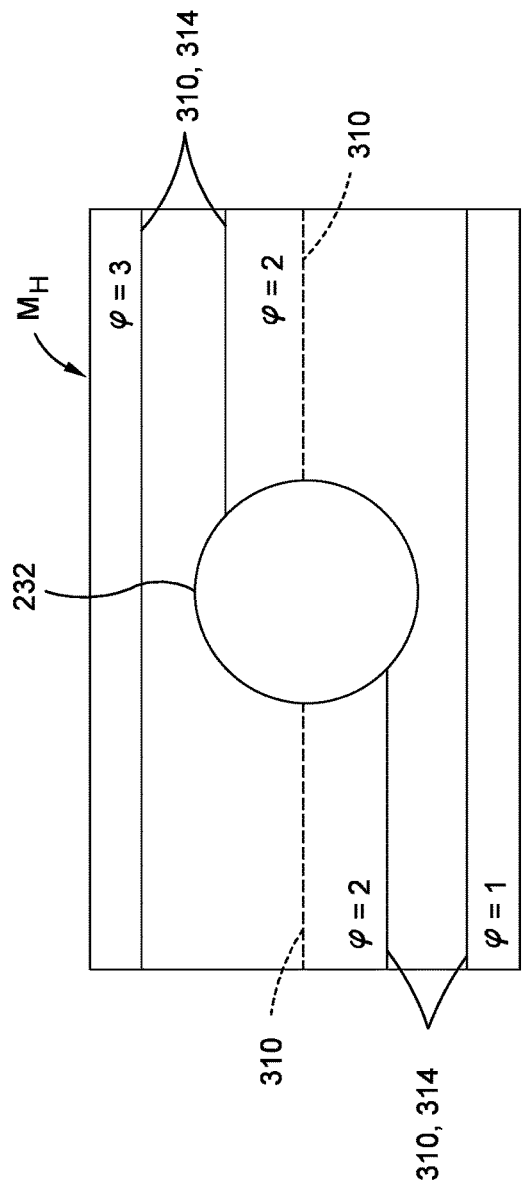
FIG. 23 is a top view of an example of a non-simply connected surface having a hole causing a discontinuity in a contour line determined by the presently-disclosed method.
Figure 24:
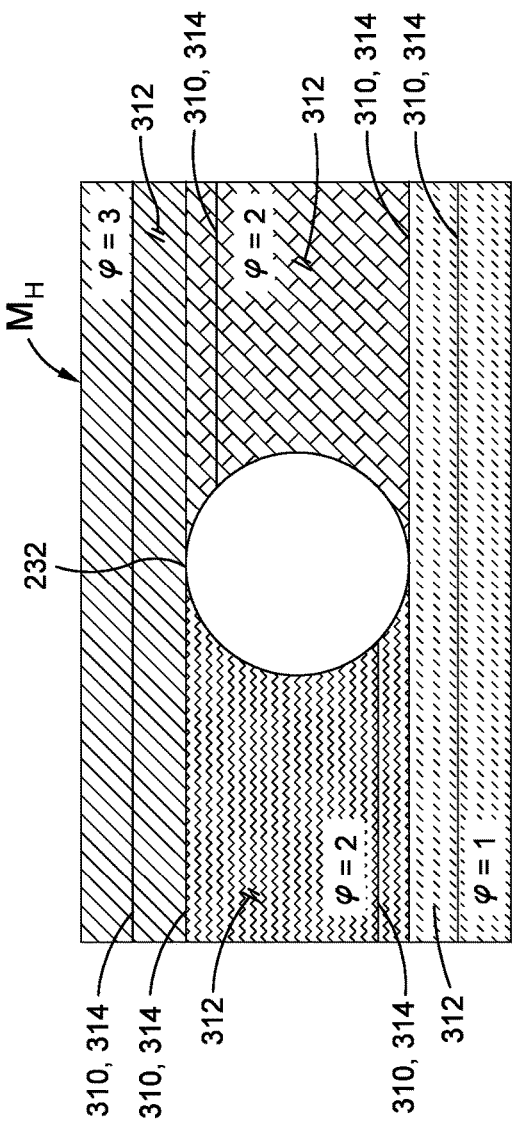
FIG. 24 is a top view of an example of the non-simply connected surface of FIG. 23 wherein the surface is partitioned into regions on which the potential function has connected contour lines.

Referring to FIGS. 23-24, shown in each figure is an example of a surface configuration for which the above-described potential fitting step and/or normalization step may also fail unless additional measures are taken. FIGS. 23-24 each show a non-simply connected surface having a hole 232 which causes a disconnected contour line 310 for the potential function φ with value 2. Normalization will find a single scaling value for both components or segments of the contour line 310 with value 2. However, to achieve best results, two scaling values are needed, one for each component of the contour line 310. A disconnected contour line may also occur in a surface (not shown) having a concave portion along a boundary of the surface. For example, a concave portion (not shown) in a surface boundary may cause a break in a contour line, resulting in two or more components of the disconnected contour line. Typically the manufacturing layup surface (e.g., of a layup tool) is larger than the composite part. If any portion of a course that follows the disconnected contour line falls within the manufacturing layup surface, then the two components of the contour line need to be treated (i.e., normalized or spaced) as the same, so that it is possible to lay down (e.g., using an AFPM) a single, continuous course in which multiple tows (FIG. 19) that make up the course are continuous. If any portion of a course that follows the disconnected contour line falls outside of the manufacturing layup surface, then the two components of the contour line may be treated (i.e., normalized or spaced) independently. However, in the example of a hole in a composite part (e.g., FIGS. 23-24), it may be undesirable to treat (e.g., normalize or space) the two components of a contour line independently because the components must be aligned so that the courses on opposite sides of the hole have the desired spacing. In addition, it may by undesirable to temporarily lift the applicator head (FIG. 19) of an AFPM from the manufacturing layup surface as the applicator head moves across a hole in the composite part, thereby requiring a smooth fiber path in which the contour line components on opposite sides of the hole are aligned.

FIG. 24 illustrates a solution to the disconnected contour line 310 (i.e., fiber path 314) by partitioning the surface into multiple regions 312 along contour lines 310 of the potential function φ such that all contour lines 310 within each region 312 are connected. The surface in FIG. 24 is partitioned using fiber paths 314 (i.e., contour lines 310) that are tangent to the hole 232 at the top side and the bottom side of the hole 232, resulting in four different regions 312 respectively represented by the four different types of cross-hatching shown in FIG. 24. Normalization of the potential function φ may be performed on a region-by-region basis. However, in the case that two components of a contour line 310 (i.e., a fiber path 314) are sufficiently close to each other (i.e., end-to-end), then it may be undesirable to consider the components as two separate contour lines. For example it would be most desirable to reposition the φ=2 contour line of FIG. 23 to the location of the dotted line 310 and maintain the identification of the φ=2 contour line across the hole 232.

Performing the additional step of smoothing may remedy the problem of a discontinuity or disconnection in one or more fiber paths 314 (i.e., contour lines 310) across a surface. Smoothing may be described as encouraging the change in magnitude of the gradient to be as small as possible. Smoothing may involve minimizing the variation in the magnitude of the gradient of the potential function φ. The potential function φ for which smoothing may be performed may be the above-described first potential function $\varphi_H$, the second potential function $\varphi_I$ (integrating factors optimization), or the third potential function $\varphi_A$ (angle optimization).

The mathematical formulation of smoothing may be introduced by recalling that the problem of determining the best solution to Equation 102 contains two components: (1) determining a potential function φ whose contour lines 310 (i.e., fiber paths 314) match the fiber directions (i.e., fiber angles 306—FIG. 10A) specified in the fiber angle definition 226 for the composite ply 202 and, (2) determining an optimal spacing 316 of the fiber paths 314 as a means to improve manufacturability of the composite ply 202. If a potential function φ exists whose gradient matches the desired vector field directions (i.e., the fiber angle definition 226) and the sets $\varphi^{-1}(c)$ are connected, then it is possible to determine an optimal fiber path spacing 316 (e.g., FIG. 16) by computing an appropriate univariate function h as in Equation 103. In this case, the above-mentioned two components to finding solutions to Equation 102 can be approached independently. Alternatively, if there is a set $\varphi^{-1}(c)$ that is not connected, then it may not be possible to correct undesirable behavior in the gradient magnitude with a univariate scaling function. For example, in FIG. 23, it can be seen that the contour line φ=2 is disconnected in the embedding space. It is not possible to re-align the disconnected contour line segments φ=2 using the scaling function h: $\mathbb{R} \to \mathbb{R}$.

However, as mentioned above, the problem of disconnected or discontinuous contour lines 310 can be remedied by partitioning a domain (i.e., a surface) into regions 312 on which $\varphi^{-1}(c)$ is connected as shown in FIG. 24 and described above, and computing scaling functions for each region 312. As an alternative to domain partitioning, the problem of disconnected contour lines 310 can be ameliorated in some cases by introducing a gradient magnitude smoothing summand into the potential fitting optimization objectives including either integral factors optimization or angle optimization. Essentially, we ask that the fits match the given vector field directions (i.e., the fiber angle definition 226) and have gradient magnitudes that vary as little as possible. In FIG. 23, the magnitude of the shown potential function φ varies more than the magnitude of the potential with evenly-spaced contours such that, with an appropriate smoothing term, fits will be moved toward the uniformly-spaced solution.

The goal of smoothing a potential function φ is to dampen variation in $\|\nabla\varphi\|\epsilon\overline{S}_h$. An operator $\overline{\nabla}$ on $\overline{S}_h$ can be defined that measures the change in a simplex-wise constant function among simplex neighbors. Let $m_k$ for $k\in\{0, 1, 2\}$ be the midpoint of the k-th edge of the triangle 220 $t_j$, and let $c_j$ be the centroid of $t_j$. Furthermore, let $S_k$ be the triangle 220 formed by $m_{k+1}$, $m_{k+2}$ and $c_j$, using mod 3 index arithmetic. The desired operator on $t_j$ is defined as the average of the gradient operators on the triangles 220 $s_0$, $s_1$ and $s_2$, where the value of a function in $\overline{S}_h$ on $m_k$ is its value on the triangle 220 adjacent to $t_j$ across the k-th edge. Therefore, the operator $\overline{\nabla}$ can be expressed as:

$$\overline{\nabla}_j = \frac{1}{3}\sum_{k=0}^{2} \nabla_{s_k} \qquad \text{(Equation 127)}$$

In Equation 127, $\nabla_{s_k}$ is the gradient operator restricted to the triangle $s_k$. These formulas (i.e., Equation 127 for each triangle j) can be assembled into a single sparse 2n by n matrix $\overline{\nabla}$. With the operator $\overline{\nabla}$ in hand, the following definition of a smoothing term $g_{smo}$ can be added as a summand to the objective functions in Equation 111 or Equation 115:

$$g_{smo} = \sum_{j=0}^{n-1} \|\overline{\nabla}_j\|\nabla\varphi\|^2\|^2 \qquad \text{(Equation 128)}$$

$$= \|\overline{\nabla}J(\nabla\varphi*\nabla\varphi)\|^2 \qquad \text{(Equation 129)}$$

wherein * denotes coordinate-wise multiplication and J is the n×2n matrix with $$(J)_{ij} = \begin{cases} 1 & j = 2(i-1)+1 \text{ or } j = 2(i-1)+2 \\ 0 & \text{otherwise} \end{cases} \qquad \text{(Equation 130)}$$

Multiplication by J on the left side of Equation 130 adds consecutive even-odd row pairs. The derivative is as follows:

$$\frac{dg_{smo}}{d\varphi} = 4(\nabla\varphi*\nabla\varphi)^T J^T \overline{\nabla}^T \overline{\nabla} J(\nabla\varphi*\nabla) \qquad \text{(Equation 131)}$$

wherein $\nabla\varphi*\nabla$ is multiplication of the rows of $\nabla$ by the corresponding coordinates of $\nabla\varphi$. The above-noted two components of determining solutions to Equation 102 can be approached independently if domain partitioning has occurred, although in practice, it is often enough to apply the smoothing heuristic.

Figures 25, 26:
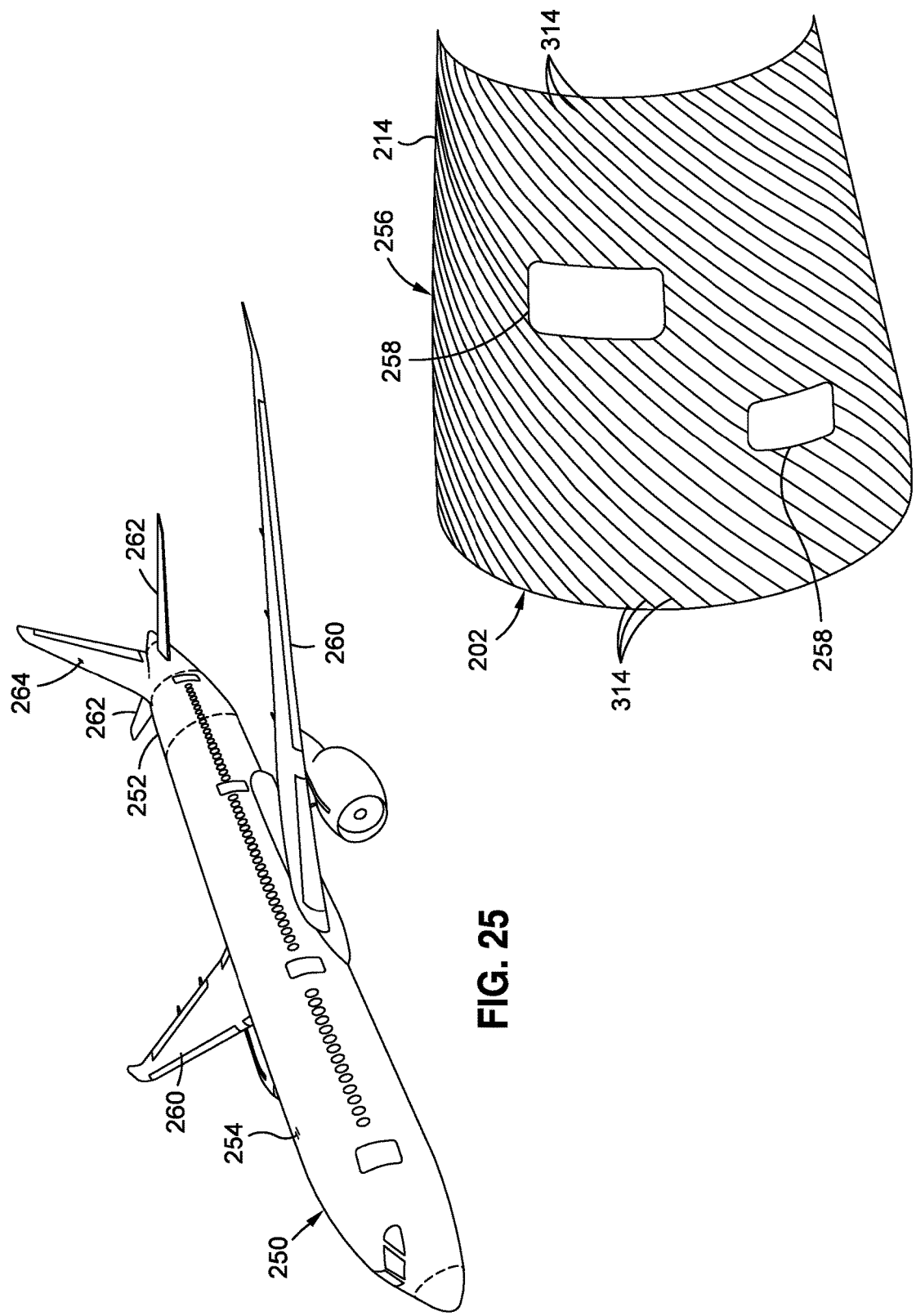
FIG. 25 is a perspective view of an example of an aircraft having one or more composite structures manufactured in a process implementing the presently-disclosed system and method.
FIG. 26 is a perspective view of an example of a composite ply of a composite fuselage skin of the aircraft of FIG. 25 and illustrating fiber paths for laying up the composite ply with a constant 45° fiber angle distribution.

FIG. 25 is a perspective view of an aircraft 250 which may include one or more composite structures 252 that may be manufactured in a process implementing the presently-disclosed system 500 and method 100 for determining fiber paths 314 for laying up composite plies 202 of a composite structure 252. For example, the composite structures 252 may include a section of a fuselage 254, a component of a wing 260, a horizontal tail 262, a vertical tail 264, or any one of a variety of other aircraft structures. FIG. 26 shows an example of a composite ply 202 of a composite fuselage skin 256 of the aircraft 250. The surface definition 214 of the fuselage skin 256 is non-simply connected due to the door cutouts 258 in the fuselage skin 256, and therefore may require smoothing fits or domain partitioning as described above. FIG. 26 shows the fiber paths 314 determined by the presently-disclosed method 100 for a constant 45° fiber angle definition specified for one or more of the composite plies 202 of the fuselage skin 256.

Figure 27:
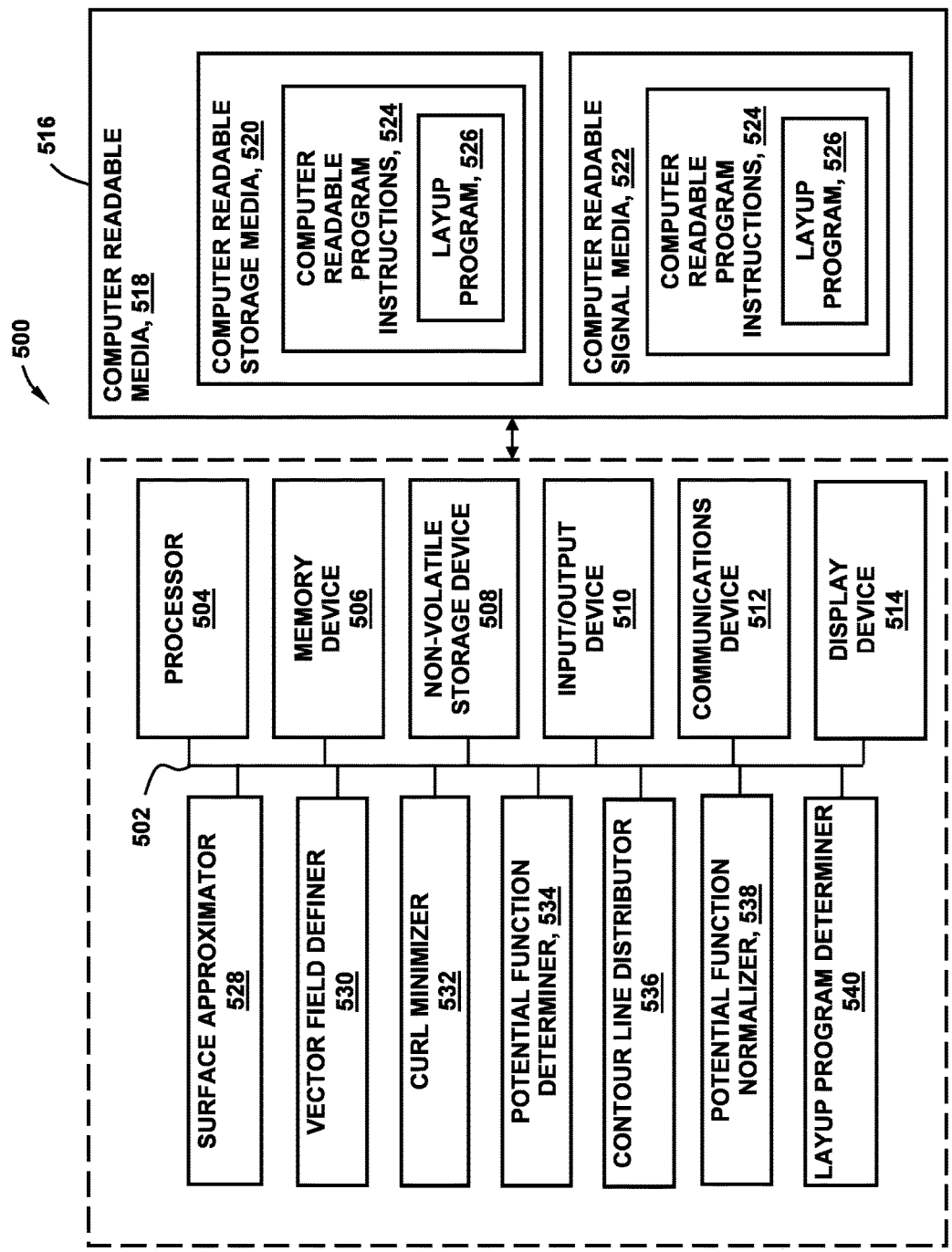
FIG. 27 is a block diagram of an example of a processor-based system for implementing one or more operations of the presently-disclosed method for determining the direction and spacing of fiber paths for a composite ply.

Referring now to FIG. 27, the above-described method 100, in whole or in part, may be performed in a computer-implemented process such as on a processor-based system 500 or other suitable computer system. The processor-based system 500 may perform computer readable program instructions 524. The computer readable program instructions 524 may be provided to or loaded onto the processor-based system 500 in order to implement one or more of the above-described operations or steps. In a non-limiting example, the processor-based system 500 and/or the computer readable program instructions 524 may facilitate the determination of the direction and spacing 316 of fiber paths 314 for a composite ply 202 given a surface definition 214 and a fiber angle definition 226 of the composite ply 202.

The block diagram of FIG. 27 illustrates the processor-based system 500 in an advantageous embodiment for determining the direction and spacing 316 of fiber paths 314. The processor-based system 500 may include a data communication path 502 (e.g., a data link) to communicatively couple one or more components to facilitate transfer of data between such components. The communication path 502 may comprise one or more data buses or any other suitable communication path that facilitates the transfer of data between the components and devices of the processor-based system 500. In a non-limiting embodiment, the components may include one or more of a processor 504, a memory device 506, a non-volatile storage device 508, a communications device 512, an input/output device 510, a display device 514, a surface approximator 528, a vector field definer 530, a curl minimizer 532, a potential function determiner 534, a contour line distributor 536 including a potential function normalizer 538, and a layup program determiner 540.

The surface approximator 528 is configured to generate a surface approximation $M_h$ of the composite ply 202 comprising a triangulated surface 218 (FIG. 8). The triangulated surface 218 includes a mesh of triangles 220 representing the surface definition 214. As mentioned above, the composite ply 202 has at least one of the following characteristics: the surface definition 214 (FIG. 6) has a non-planar contour 222 and/or the fiber angle definition 226 (FIG. 7) comprises non-constant fiber angles 230. The surface approximator 528 may include a mesh generator (not shown) to generate the triangulated surface 218 of the composite ply 202. The surface approximator 528 may generate the triangulated surface 218 based on the surface definition 214 of the composite ply 202 as may be represented by a computer-aided-design model (not shown) of the composite ply 202. Alternately, a user may import the triangulated surface 218 of the composite ply 202 by using the input/output device 510.

The vector field definer 530 is configured to define on the triangulated surface 218 the first unit vector field $X^0$ (FIG. 9) establishing a 0-degree direction 302 for each one of the triangles 220. As mentioned above, the 0-degree direction 302 is the direction from which the fiber angles are measured. In some examples, the vector field definer 530 may establish the first unit vector field $X^0$ by projecting a physical space rosette vector onto each triangulated surface 218 as shown in FIG. 9A. Alternatively, as mentioned above, the vector field definer 530 may establish the first unit vector field $X^0$ by using the gradient vector field (not shown) of a function defined on the surface, or the vector field definer 530 may establish the first unit vector field $X^0$ by evaluating a function that describes the direction of the vector field as a function of surface coordinates.

The vector field definer 530 is configured to define on the triangulated surface 218 a second unit vector field X (FIG. 10) by rotating, through the fiber angles specified (e.g., by a structural design engineer), the first unit vector field $X^0$ about surface normals 304 respectively corresponding to the triangles 220. For example, FIG. 10A illustrates a first unit vector rotated through the fiber angle specified for the location of the surface normal 304 in the triangle 220. The vector field definer 530 may establish the second unit vector field X based on a fiber angle definition 226 comprising constant ply angles (e.g., FIG. 4) or based on a fiber angle definition 226 comprising non-constant ply angles (e.g., FIG. 5). In some examples, the vector field definer 530 may establish the second unit vector field X based on a fiber angle definition 226 originating from a function of surface coordinates (not shown) of the triangulated surface 218.

The vector field definer 530 is also configured to determine the direction of the gradient of a potential function $\varphi$, the contour lines 310 of which match the fiber directions (e.g., fiber angles) as defined by the fiber angle definition 226 specified for the composite ply 202 and the laminate reference direction represented by the first unit vector field $X^0$. In this regard, the vector field definer 530 is configured to define on the triangulated surface 218 a third unit vector field Y (FIG. 11) representing the direction of a gradient of the potential function $\varphi$, by rotating the second unit vector field X over 90° about the respective surface normals 304. For example, FIG. 11A shows the rotation of a second unit vector over 90° about a surface normal 304 of a triangle 220.

The curl minimizer 532 is configured to determine a magnitude function $f$ to scale the third unit vector field $\overline{Y}$ over the triangulated surface 218 to create a non-unit vector field Y (FIG. 12) to enable fitting the potential function $\varphi$ to the second unit vector field X, by minimizing the curl of the non-unit vector field Y. FIG. 12A shows a non-unit vector Y of one of the triangles 220 scaled according to the magnitude function $f$ as described above.

The potential function determiner 534 is configured to determine a first potential function $\varphi_H$ of the composite ply 202. The first potential function $\varphi_H$ (FIG. 13) has contour lines 310 that represent fiber paths 314 approximating the fiber angle distribution corresponding to the second unit vector field X. As described above, the first potential function $\varphi_H$ is determined by performing a least-squares fit such that the direction and magnitude of the gradient of the first potential function $\varphi_H$ best approximate the direction and the magnitude function $f$ of the non-unit vector field Y on the triangulated surface 218. As is also described above, the potential function determiner 534 may optionally perform an integrating factors optimization to refine the first potential function $\varphi_H$ into a second potential function $\varphi_I$ (FIG. 14) that provides improved alignment of the contour lines 310 with the second unit vector field X. In this regard, the potential function determiner 534 may minimize the deviation between the direction of the non-unit vector field Y and the gradient direction of the second potential function $\varphi_I$, while also adjusting the magnitude function scaling $f$ of the third unit vector field $\overline{Y}$. The potential function determiner 534 may also optionally refine either the first potential function $\varphi_H$ or the second potential function $\varphi_I$ using angle optimization as described above to determine a third potential function $\varphi_A$ (FIG. 15) that improves the alignment of the contour lines 310 with the second unit vector field X by minimizing only the deviation between the direction of the third unit vector field $\overline{Y}$ and the gradient direction of the potential function $\varphi$, and disregarding the scaling function $f$, the inverse of which defines the spacing 316 between the contour lines 310 of the potential function $\varphi$.

The contour line distributor 536 is configured to distribute the contour lines 310 of the potential function $\varphi$ (e.g., the first potential function $\varphi_H$, the second potential function $\varphi_I$, or the third potential function $\varphi_A$) over the triangulated surface 218 such that the contour lines 310 are generally uniformly spaced and can be used as fiber paths 314 for laying courses 206 of composite tape 208 to form a composite ply 202. In an embodiment, the contour line distributor 536 may comprise a potential function normalizer 538 configured to perform a normalization of the potential function $\varphi$ (e.g., by region of the triangulated surface 218) by applying a scaling function to the potential function $\varphi$ such that the contour lines 310 are uniformly distributed across the triangulated surface 218.

The potential function normalizer 538 is optionally configured to perform an averaging normalization by applying a scaling function to the potential function $\varphi$ that adjusts the value of the magnitude of the gradient of p along each contour line 310 such that the magnitude of the gradient along each contour line 310 is on average equivalent to a head width 408 of an AFPM 400. Such an arrangement results in one or more pairs of adjacent courses 206 having some overlap 320 and some gaps 318 at one or more locations along the length of the pair of adjacent contour lines 310, as described above and shown in FIG. 21. Alternatively, the potential function normalizer 538 is optionally configured to perform a head width normalization by applying a scaling function to the potential function $\varphi$ that adjusts the value of the magnitude of the gradient of $\varphi$ along each contour line 310 such that the inverse of the minimum magnitude of the gradient along each contour line 310 is not greater than a head width 408 of an AFPM 400. Such an arrangement results in one or more pairs of adjacent courses 206 having some overlap 320 but no gaps 318 at one or more locations along the length of a pair of adjacent contour lines 310, as described above and shown in FIG. 22.

For a triangulated surface 218 in which at least one of the contour lines 310 is disconnected across the triangulated surface 218 (e.g., due to a hole 232—FIGS. 23-24), the contour line distributor 536 is configured to smooth the potential function $\varphi$ by minimizing the variation in the magnitude of the gradient of the potential function $\varphi$, as described above. Alternatively, the contour line distributor 536 is configured to distribute the contour lines 310 over the triangulated surface 218 by partitioning the surface (e.g., FIG. 24) into regions 312 along contour lines 310 of the potential function $\varphi$ such that all contour lines 310 within each region 312 are connected, as is also described above.

The layup program determiner 540 is configured to use the contour lines 310 of the normalized potential function ($h°\varphi$—FIG. 16) as fiber paths 314 in a layup program 526 for fabricating the composite ply 202 by laying up courses 206 of composite tape 208. If the above-described head width normalization is used and overlaps 320 (FIGS. 21-22) are undesired, then the gradient information may be used to provide a first estimate of the number of tows 204 (FIG. 19) needed at different locations along a fiber path 314 (e.g., the course centerline) to allow the AFPM 400 to adjust the course width by cutting and adding tows 204 from the side edges of the composite tape 208. The layup program 526 may be output to an AFPM 400 (FIGS. 19-22) which includes an applicator head 406 configured to align the centerline 410 (FIG. 20) of the applicator head 406 with contour lines 310 (e.g., fiber paths) when laying up courses 206 (e.g., composite tape 208) onto a substrate 210. The AFPM 400 may lay up a plurality of composite plies 202 on top of each other according to a predetermined stacking sequence to fabricate a composite layup for subsequent processing (e.g., curing) to form a composite laminate 200 (FIGS. 2-3).

The display device 514 may receive and display the above-mentioned surface definition 214 (FIG. 6), the fiber angle definition 226 (FIG. 7), the surface approximation (e.g., the triangulated surface 218—FIG. 8) of the composite ply 202, the first unit vector field $X^0$ (FIG. 9), the second unit vector field X (FIG. 10), the third unit vector field $\overline{Y}$ (FIG. 11), the non-unit vector field Y (FIG. 12), the first potential function $\varphi_H$ (FIG. 13), the second potential function $\varphi_I$ (FIG. 14), the third potential function $\varphi_A$ (FIG. 15), and the normalized potential function (h°$\varphi$—FIG. 16). The display device 514 may receive the above-noted data from one or more of the corresponding components of the processor-based system 500 via the communication path 502. The display device 514 may display the values as a graphical display and/or as numerical values.

In an embodiment, the processor-based system 500 may include one or more of the processors 504 for executing instructions of computer readable program instructions 524 that may be installed into the memory device 506. Alternatively, a processor 504 may comprise a multi-processor core having two or more integrated processor cores. Even further, the processor 504 may comprise a main processor and one or more secondary processors integrated on a chip. The processor 504 may also comprise a multi-processor system having a plurality of similarly configured processors.

Referring still to FIG. 27, the processor-based system 500 may further include one or more memory devices 506 which may comprise one or more of volatile or non-volatile storage devices 508. However, the memory device 506 may comprise any hardware device for storing data. For example, the memory device 506 may comprise a random access memory or a cache of an interface and/or integrated memory controller hub which may be included in the communication path 502. The memory device 506 may be configured to permanently and/or temporarily store any one of a variety of different types of data, computer readable code or program instructions 524, or any other type of information. The non-volatile storage device 508 may be provided in a variety of configurations including, but not limited to, a flash memory device, a hard drive, an optical disk, a hard disk, a magnetic tape or any other suitable embodiment for long-term storage. In addition, the non-volatile storage device 508 may comprise a removable device such as a removable hard drive.

The processor-based system 500 may additionally include one or more of the input/output devices 510 to facilitate the transfer of data between components that may be connected to the processor-based system 500. An input/output device 510 may be directly and/or indirectly coupled to the processor-based system 500. The input/output device 510 may facilitate user-input by means of a peripheral device such as a keyboard, a mouse, a joystick, a touch screen and any other suitable device for inputting data to the processor-based system 500. The input/output device 510 may further include an output device for transferring data representative of the output of the processor-based system 500. For example the input/output device 510 may comprise a display device 514 such as a computer monitor or computer screen for displaying results of data processed by the processor-based system 500. The input/output device 510 may optionally include a printer or fax machine for printing a hardcopy of information processed by the processor-based system 500.

Referring still to FIG. 27, the processor-based system 500 may include one or more communications devices 512 to facilitate communication of the processor-based system 500 within a computer network and/or with other processor-based systems. Communication of the processor-based system 500 with a computer network or with other processor-based systems may be by wireless means and/or by hardwire connection. For example, the communications device 512 may comprise a network interface controller to enable wireless or cable communication between the processor-based system 500 and a computer network. The communications device 512 may also comprise a modem and/or a network adapter or any one of a variety of alternative devices for transmitting and receiving data.

One or more of the operations of the above-described method 100 for determining the direction and spacing 316 of fiber paths 314 for a composite ply 202 may be performed by the processor 504 and/or by one or more of the surface approximator 528, the vector field definer 530, the curl minimizer 532, the potential function determiner 534, the contour line distributor 536, the potential function normalizer 538, and the layup program determiner 540 using the computer readable program instructions 524. The computer readable program instructions 524 may comprise program code which may include computer usable program code and computer readable program code. The computer readable program instructions 524 may be read and executed by the processor 504. The computer readable program instructions 524 may enable the processor 504 to perform one or more operations of the above-described embodiments associated with determining the direction and spacing 316 of fiber paths 314 for a composite ply 202.

Referring still to FIG. 27, the computer readable program instructions 524 may include operating instructions for the processor-based system 500 and may further include applications and programs. The computer readable program instructions 524 may be contained and/or loaded onto one or more of memory devices 506 and/or non-volatile storage devices 508 for execution by the processor 504 and/or by the surface approximator 528, the vector field definer 530, the curl minimizer 532, the potential function determiner 534, the contour line distributor 536, the potential function normalizer 538, and the layup program determiner 540. As indicated above, one or more of the memory devices 506 and/or non-volatile storage devices 508 may be communicatively coupled to one or more of the remaining components illustrated in FIG. 27 through the communication path 502.

The computer readable program instructions 524 may be contained on tangible or non-tangible, transitory or non-transitory computer readable media 518 and which may be loaded onto or transferred to the processor-based system 500 for execution by the processor 504. The computer readable program instructions 524 and the computer readable media 518 comprise a computer program product 516. In an embodiment, the computer readable media 518 may comprise computer readable storage media 520 and/or computer readable signal media 522.

The computer readable storage media 520 may comprise a variety of different embodiments including, but not limited to, optical disks and magnetic disks that may be loaded into a drive, a flash memory device or other storage device or hardware for transfer of data onto a storage device such as a hard drive. The computer readable storage media 520 may be non-removably installed on the processor-based system 500. The computer readable storage media 520 may comprise any suitable storage media and may include, without limitation, a semiconductor system or a propagation medium. In this regard, the computer readable storage media 520 may comprise electronic media, magnetic media, optical media, electromagnetic media, and infrared media. For example, the computer readable storage media 520 may comprise magnetic tape, a computer diskette, random access memory and read-only memory. Non-limiting examples of embodiments of optical disks may include compact disks—read only memory, compact disks—read/write, and digital video disks.

The computer readable signal media 522 may contain the computer readable program instructions 524 and may be embodied in a variety of data signal configurations including, but not limited to, an electromagnetic signal and an optical signal. Such data signals may be transmitted by any suitable communications link including by wireless or hardwire means. For example, the hardwire means may comprise an optical fiber cable, a coaxial cable, a signal wire and any other suitable means for transmitting the data by wireless or by physical means.

Referring still to FIG. 27, the computer readable signal media 522 may facilitate the downloading of the computer readable program instructions 524 to the non-volatile storage or other suitable storage or memory device for use within processor-based system 500. For example, the computer readable program instructions 524 contained within the computer readable storage media 520 may be downloaded to the processor-based system 500 over a computer network from a server or client computer of another system.

Any one of a variety of different embodiments of the processor-based system 500 may be implemented using any hardware device or system capable of executing the computer readable program instructions 524. For example, the processor 504 may comprise a hardware unit configured for performing one or more particular functions wherein the computer readable program instructions 524 for performing the functions may be pre-loaded into the memory device 506.

In an embodiment, the processor 504 may comprise an application specific integrated circuit (ASIC), a programmable logic device, or any other hardware device configured to perform one or more specific functions or operations. For example, a programmable logic device may be temporarily or permanently programmed to perform one or more of the operations related to determining a potential function φ, optimizing a potential function φ, and/or performing a normalization of a potential function φ. The programmable logic device may comprise a programmable logic array, programmable array logic, a field programmable logic array, and a field programmable gate array and any other suitable logic device, without limitation. In an embodiment, the computer readable program instructions 524 may be operated by the one or more processor 504 and/or by other devices including one or more hardware units in communication with the processor 504. Certain portions of the computer readable program instructions 524 may be the processor 504 and other portions of the computer readable program instructions 524 may be run by the hardware units.

Advantageously, the various embodiments described above provide the ability to determine fiber paths 314 that match the fiber angle definition 226 specified for a composite ply 202, while also providing the ability to optimize the spacing 316 of the fiber paths 314 by quantifying convergence and/or divergence of such fiber paths 314. The technical effect of performing the above-described method 100 is the ability to predict overlaps 320 and gaps 318 between courses 206 which may negatively impact the structural properties (e.g., strength and stiffness) and/or the surface quality of a composite laminate 200 made up of composite plies 202. A further technical effect of the above-described method 100 is design engineers have the ability to predict and consider the effects of convergence and divergence on the manufacturability of a composite laminate, and thereby avoid expensive and time-consuming rework that may otherwise be required during manufacturing of composite laminate 200 to compensate for overlaps 320 and/or gaps 318 between courses 206 of a composite ply 202. An additional technical effect of performing the above-described method 100 is that convergence and divergence can be considered during the design stage of a composite laminate 200, thereby allowing a wider range of designs to be considered including designs that may be more efficient in terms of strength and/or stiffness. Furthermore, the above-described method 100 allow for the number of courses to be predicted without performing full numerical control (NC) programming of an AFPM, allowing different designs to be compared.

Many modifications and other configurations of the disclosure will come to mind to one skilled in the art, to which this disclosure pertains, having the benefit of the teachings presented in the foregoing descriptions and the associated drawings. The configurations described herein are meant to be illustrative and are not intended to be limiting or exhaustive. Although specific terms are employed herein, they are used in a generic and descriptive sense only and not for purposes of limitation.

What is claimed is:

1. A method of determining a direction and spacing of fiber paths for a composite ply of a composite layup given a surface definition and a fiber angle definition having one or more fiber angles, comprising the steps of:

generating an approximation of the surface, the approximation comprising a triangulated surface including a mesh of triangles, the composite ply having at least one of the following characteristics: the surface definition has a non-planar contour, the fiber angle definition comprises non-constant fiber angles;

defining on the triangulated surface a first unit vector field establishing a 0-degree direction for each one of the triangles, the 0-degree direction being the direction from which the one or more fiber angles are measured;

defining on the triangulated surface a second unit vector field by rotating, through the one or more fiber angles specified in the fiber angle definition, the first unit vector field about surface normals respectively corresponding to the triangles;

defining on the triangulated surface a third unit vector field comprising vectors each having a length of one and representing a direction of a gradient of a first potential function to be determined, the third unit vector field being defined on the triangulated surface by rotating the second unit vector field 90° about the respective surface normals in preparation for determining the first potential function, the direction of the gradient being perpendicular to the direction of the fiber paths to be defined as a result of determining the first potential function;

determining a magnitude function to scale the third unit vector field over the triangulated surface to create a non-unit vector field that enables solving for the first potential function in a manner accounting for an interdependence of direction and magnitude of the gradient, wherein determining the magnitude function comprises determining, for each vector in the third unit vector field, a length that represents a relative spacing of the fiber paths, and searching all non-zero lengths of the vectors of the non-unit vector field and selecting the vectors of non-zero length that make a curl of the non-unit vector field as small as possible, wherein the selected vectors of non-zero length correspond to the magnitude function;

determining the first potential function by performing a least-squares fit of the direction and magnitude of the gradient of the first potential function to the direction and magnitude of the non-unit vector field, the first potential function having contour lines that comprise epuipotential lines which are aligned with the second unit vector field;

performing a normalization of the first potential function by applying a scaling function to the first potential function such that the contour lines are uniformly distributed across the triangulated surface; and using the contour lines of the normalized potential function as fiber paths for laying up courses of composite material along the fiber paths to fabricate the composite ply.

2. The method of claim 1, further including the step of:
determining a second potential function that improves alignment of the contour lines with the second unit vector field by minimizing deviation between the direction of the non-unit vector field and the gradient direction of the first potential function, while also adjusting the magnitude function scaling the third unit vector field.

3. The method of claim 1, further including the step of:
determining a third potential function that improves alignment of the contour lines with the second unit vector field by minimizing only deviation between the direction of the third unit vector field and the gradient direction of the first potential function.

4. The method of claim 1, wherein, in the step of defining the second unit vector field on the triangulated surface:
the fiber angle definition comprises constant ply angles.

5. The method of claim 1, further including:
smoothing the first potential function by minimizing variation in the magnitude of the gradient of the first potential function.

6. The method of claim 1, wherein the contour lines are disconnected across the triangulated surface and, after determining the first potential function, the method further includes:
partitioning the surface approximation into regions along contour lines of the first potential function such that all contour lines within each region are connected.

7. The method of claim 1, wherein the step of performing a normalization of the first potential function comprises:
applying a scaling function to the first potential function to adjust values of the first potential function such that an inverse of the magnitude of the gradient along each contour line is on average equivalent to a head width of an automated fiber placement machine.

8. The method of claim 1, wherein the step of performing a normalization of the first potential function comprises:
applying a scaling function to the first potential function to adjust values of the first potential function such that an inverse of the minimum magnitude of the gradient along each contour line is not greater than a head width of an automated fiber placement machine to avoid gaps between adjacent courses.

9. The method of claim 1, wherein the contour lines of the normalized potential function have a spacing, the method further including the step of:
adjusting a width of one or more of the courses to be less than the spacing between the contour lines to avoid overlapping of adjacent courses.

10. A method of determining a direction and spacing of fiber paths for a composite ply of a composite layup given a surface definition and a fiber angle definition having one or more fiber angles, comprising the steps of:

generating an approximation of the surface, the approximation comprising a triangulated surface including a mesh of triangles, the composite ply having at least one of the following characteristics: the surface definition has a non-planar contour, the fiber angle definition comprises non-constant fiber angles;

defining on the triangulated surface a first unit vector field establishing a 0-degree direction for each one of the triangles, the 0-degree direction being the direction from which the one or more fiber angles are measured;

defining on the triangulated surface a second unit vector field by rotating, through the one or more fiber angles specified in the fiber angle definition, the first unit vector field about surface normals respectively corresponding to the triangles;

defining on the triangulated surface a third unit vector field comprising vectors each having a length of one and representing a direction of a gradient of a first potential function to be determined, the third unit vector field being defined on the triangulated surface by rotating the second unit vector field 90° about the respective surface normals in preparation for determining the first potential function, the direction of the gradient being perpendicular to the direction of the fiber paths to be defined as a result of determining the first potential function;

determining a magnitude function to scale the third unit vector field over the triangulated surface to create a non-unit vector field that enables solving for the first potential function in a manner accounting for an interdependence of direction and magnitude of the gradient, wherein determining the magnitude function comprises determining, for each vector in the third unit vector field, a length that represents a relative spacing of the fiber paths, and searching all non-zero lengths of the vectors of the non-unit vector field and selecting the vectors of non-zero length that make a curl of the non-unit vector field as small as possible, wherein the selected vectors of non-zero length correspond to the magnitude function;

determining the first potential function by performing a least-squares fit of the direction and magnitude of the gradient of the first potential function to the direction and magnitude of the non-unit vector field, the first potential function having contour lines that comprise lines which are aligned with the second unit vector field;

performing a normalization of the first potential function by applying a scaling function to the first potential function such that the contour lines are uniformly distributed across the triangulated surface; and using the contour lines of the normalized potential function as fiber paths in a layup program that is output to an automated fiber placement machine having an applicator head configured to layup courses of composite tape along the fiber paths.

11. A processor-based system for determining a direction and spacing of fiber paths for a composite ply of a composite layup given a surface definition of the composite ply and a fiber angle definition having one or more fiber angles, comprising:

a surface approximator configured to generate an approximation of the surface of the composite ply, the approximation comprising a triangulated surface including a mesh of triangles representing the surface definition, the composite ply having at least one of the following characteristics: the surface definition has a non-planar contour, the fiber angle definition comprises non-constant fiber angles;

a vector field definer configured to:
define on the triangulated surface a first unit vector field establishing a 0-degree direction for each one of the triangles, the 0-degree direction being the direction from which the one or more fiber angles are measured;
define on the triangulated surface a second unit vector field by rotating, through the one or more fiber angles specified in the fiber angle definition, the first unit vector field about surface normals respectively corresponding to the triangles;
define on the triangulated surface a third unit vector field comprising vectors each having a length of one and representing a direction of a gradient of a first potential function to be determined, the third unit vector field being defined on the triangulated surface by rotating the second unit vector field 90° about the respective surface normals in preparation for determining the first potential function, the direction of the gradient being perpendicular to the direction of the fiber paths to be defined as a result of determining the first potential function;

a curl minimizer configured to determine a magnitude function to scale the third unit vector field over the triangulated surface to create a non-unit vector field that enables solving for the first in a manner accounting for an interdependence of direction and magnitude of the gradient, wherein determining the magnitude function comprises determining, for each vector in the third unit vector field, a length that represents a relative spacing of the fiber paths, and searching all non-zero lengths of the vectors of the non-unit vector field and selecting the vectors of non-zero length that make a curl of the non-unit vector field as small as possible, wherein the selected vectors of non-zero length correspond to the magnitude function;

a potential function determiner configured to determine the first potential function by performing a least-squares fit of the direction and magnitude of the gradient of the first potential function to the direction and magnitude of the non-unit vector field on the triangulated surface, the first potential function having contour lines that comprise equipotential lines which are aligned with the second unit vector field;

a potential function normalizer configured to perform a normalization of the first potential function by applying a scaling function to the first potential function such that the contour lines are uniformly distributed across the triangulated surface by setting constant values of the first potential function that vary at fixed intervals between adjacent pairs of contour lines; and a layup program determiner configured to use the contour lines of the normalized potential function as fiber paths in a layup program for fabricating the composite ply by laying up courses of composite tape that follow the fiber paths and thereby form the composite ply.

12. The processor-based system of claim 11, wherein:
the potential function determiner is configured to determine a second potential function that improves alignment of the contour lines with the second unit vector field by minimizing a deviation between the direction of the non-unit vector field and the gradient direction of the second potential function, while also adjusting the magnitude function scaling the third unit vector field.

13. The processor-based system of claim 11, wherein:
the potential function determiner is configured to determine a third potential function that improves alignment of the contour lines with the second unit vector field by minimizing only a deviation between the direction of the third unit vector field and the gradient direction of the first potential function.

14. The processor-based system of claim 11, wherein:
the vector field definer is configured to establish the first unit vector field by projecting a physical space rosette vector onto the triangulated surface.

15. The processor-based system of claim 11, wherein:
the vector field definer is configured to establish the second unit vector field on the triangulated surface based on a fiber angle definition comprising constant ply angles.

16. The processor-based system of claim 11, wherein:
the vector field definer is configured to establish the second unit vector field on the triangulated surface based on a fiber angle definition originating from a function of surface coordinates of the triangulated surface.

17. The processor-based system of claim 11, wherein:
at least one of the contour lines is disconnected across the triangulated surface; and
the potential function normalizer is configured to smooth the first potential function by minimizing variation in the magnitude of the gradient of the first potential function.

18. The processor-based system of claim 11, wherein:
at least one of the contour lines is disconnected across the triangulated surface; and
the potential function normalizer is configured to distribute the contour lines over the triangulated surface by partitioning the surface approximation into regions along contour lines of the first potential function such that all contour lines within each region are connected.

19. The processor-based system of claim 11, wherein:
the potential function normalizer is configured to apply a scaling function to the first potential function to adjust values of the first potential function such that an inverse of the magnitude of the gradient along each contour line is on average equivalent to a head width of an automated fiber placement machine.

20. The processor-based system of claim 11, wherein:
the potential function normalizer is configured to apply a scaling function to the first potential function to adjust values of the first potential function such that an inverse of the minimum magnitude of the gradient along each contour line is not greater than a head width of an automated fiber placement machine.

* * * * *